(12) United States Patent
Wager et al.

(10) Patent No.: US 10,881,322 B2
(45) Date of Patent: Jan. 5, 2021

(54) NEUROPHYSIOLOGICAL SIGNATURES FOR FIBROMYALGIA

(71) Applicant: The Regents of the University of Colorado, a body corporate, Denver, CO (US)

(72) Inventors: Tor Wager, Boulder, CO (US); Marina Lopez-Sola, Boulder, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 454 days.

(21) Appl. No.: 15/687,358

(22) Filed: Aug. 25, 2017

(65) Prior Publication Data
US 2018/0055407 A1 Mar. 1, 2018

Related U.S. Application Data

(60) Provisional application No. 62/379,600, filed on Aug. 25, 2016.

(51) Int. Cl.
*A61B 5/055* (2006.01)
*A61B 5/00* (2006.01)
*G01R 33/48* (2006.01)

(52) U.S. Cl.
CPC ............ *A61B 5/055* (2013.01); *A61B 5/0042* (2013.01); *A61B 5/0053* (2013.01); *A61B 5/4076* (2013.01); *A61B 5/4824* (2013.01); *A61B 5/4848* (2013.01); *A61B 5/7235* (2013.01); *A61B 5/7282* (2013.01); *G01R 33/4806* (2013.01); *A61B 5/0048* (2013.01); *A61B 5/7264* (2013.01); *A61B 2576/026* (2013.01)

(58) Field of Classification Search
CPC ..... A61B 5/055; A61B 5/4076; A61B 5/4824; A61B 5/0042; A61B 5/0053; A61B 5/4848; A61B 5/7235; A61B 5/7282; A61B 5/7264; A61B 2576/026; A61B 5/0048; G01R 33/4806
See application file for complete search history.

(56) References Cited

U.S. PATENT DOCUMENTS

| | | | | |
|---|---|---|---|---|
| 7,462,155 | B2* | 12/2008 | England | A61B 5/055 600/407 |
| 7,651,459 | B2* | 1/2010 | Cameron | A61N 2/02 600/9 |
| 8,177,702 | B2* | 5/2012 | Riehl | A61B 5/6844 600/13 |
| 9,884,200 | B2* | 2/2018 | Pillutla | A61N 2/02 |

(Continued)

OTHER PUBLICATIONS

Lopez-Sola et al. "Towards a neurophysiological signature for fibromyalgia," Pain, 2017, vol. 158, No. 1, pp. 34-47.
Power et al. "Spurious but systematic correlations in functional connectivity MRI networks arise from subject motion," Neuroimage, Feb. 2012, vol. 59, No. 3, pp. 2142-2154.
(Continued)

*Primary Examiner* — Sanjay Cattungal
(74) *Attorney, Agent, or Firm* — Berg Hill Greenleaf Ruscitti LLP

(57) ABSTRACT

Described herein are novel fMRI-based neurologic signatures that predict fibromyalgia (FM), clinical severity, and treatment outcomes. Further described are methods for diagnosing FM and for predicting or evaluating efficacy of a treatment of FM based on the neurologic signature.

20 Claims, 11 Drawing Sheets

(56) References Cited

U.S. PATENT DOCUMENTS

| | | | |
|---|---|---|---|
| 2006/0004422 A1* | 1/2006 | De Ridder | A61N 1/0531 607/45 |
| 2009/0076372 A1 | 3/2009 | England | |
| 2013/0317580 A1* | 11/2013 | Simon | A61N 1/04 607/115 |
| 2014/0257438 A1* | 9/2014 | Simon | A61N 2/02 607/72 |
| 2015/0201879 A1 | 7/2015 | Hargrove | |
| 2016/0054409 A1* | 2/2016 | Wager | A61B 5/055 600/411 |

OTHER PUBLICATIONS

Pujol et al. "Mapping Brain Response to Pain in Fibromyalgia Patients Using Temporal Analysis of fMRI," PLOSone, Apr. 2009, vol. 4, No. 4, e5224, 10 pages.

Pujol et al. Does motion-related brain functional connectivity reflect both artifacts and genuine neural activity? Neuroimage, Nov. 2014, vol. 101, No. 1, pp. 87-95.

Wager et al. "Prefrontal-Subcortical Pathways Mediating Successful Emotion Regulation," Neuron, Sep. 2008, vol. 59, No. 6, pp. 1037-1050.

Wager et al. "An fMRI-Based Neurologic Signature of Physical Pain," The New England Journal of Medicine, Apr. 2013, vol. 368, No. 15, pp. 1388-1397.

International Search Report and Written Opinion for International (PCT) Patent Application No. PCT/US17/48686, dated Jan. 5, 2018 12 pages.

\* cited by examiner

NEUROPHYSIOLOGICAL SIGNATURES FOR FIBROMYALGIA

CROSS REFERENCE TO RELATED APPLICATION

This application claims the benefit of priority under 35 U.S.C. §119(e) to U.S. Provisional Patent Application Ser. No. 62/379,600, filed Aug. 25, 2016, which is incorporated herein by reference.

GOVERNMENT SUPPORT

This invention was made with government support under grant number R01 DA035484 awarded by the National Institutes of Health. The government has certain rights in the invention.

FIELD OF THE INVENTION

The present invention generally relates to the use of fMRI technology to determine a neurological signature of fibromyalgia.

BACKGROUND OF INVENTION

Fibromyalgia (FM) is characterized by the presence of widespread musculoskeletal pain and tenderness accompanied by fatigue, cognitive/emotional, and sleep-related symptoms, occurring without any other medical explanation. Besides its high prevalence and clinical relevance, there is an inherent problem associated with the diagnosis of FM, in that there is an absence of laboratory findings or well-characterized pathology that is sensitive and specific for the disorder. The existence of FM as a clinical diagnosis has been therefore historically questioned. The past two decades of research, however, have provided consistent evidence to suggest abnormal nervous system findings in patients with FM. Neuroimaging studies have shown augmented responses to a variety of painful stimuli in FM and altered brain structure, metabolic activity, and resting state functional connectivity in regions that are consistently involved in processing pain. In addition to pain-related changes, patients with FM show reduced tolerance (i.e., augmented unpleasantness) to nonpainful sensory stimulation (visual, auditory, olfactory, and tactile), along with abnormal brain processing of nonpainful sensory stimuli. Evidence suggests that the brain systems involved in the primary cortical processing of nonpainful sensory signals and their integration may play an important role in FM pain.

These studies suggest that pain in FM may be associated with (1) hyperexcitability of the nociceptive system, i.e., increased transmission, central amplification, and/or reduced inhibitory control mechanisms and (2) reduced opponent non-nociceptive sensory processing. Despite these brain and behavioral findings, there remains a critical gap between characterizing abnormalities in FM at a group level and identifying neurophysiological markers diagnostic of FM at an individual patient level.

Thus, there continues to be a need in the art for methods that are sensitive and specific to FM and can provide objective measurements of FM. This disclosure addresses such needs.

SUMMARY OF INVENTION

The inventors have used a multisensory approach to identify a brain signature sensitive to FM status (vs healthy) at the individual person level. Tests of both mechanical pain and nonpainful sensory brain responses were used to (1) characterize the sensory processing alterations that are distinctive of FM at the central level and (2) address how such characteristic pathophysiological features relate to FM patients' core symptoms.

As a first approach to assess alterations in central pain processing, the inventors applied a neurologic pain signature (NPS), a multivariate brain activation pattern that was previously validated to be sensitive and specific to predict experimental pain perception at the individual-person level (Wager T D, et al., N Engl J Med (2013) 368:1388-97; and US Patent Publication No. 2016/0054409, filed 9 Apr. 2014, incorporated herein by reference in its entirety). The NPS accurately predicts experimental pain perception but does not respond to other unpleasant, highly arousing emotional experiences. Augmented expression of the NPS in FM would indicate enhanced pain specific cerebral processing in patients. Additionally, the inventors applied cross-validated machine learning algorithms to differentiate patients with FM from healthy participants based on their brain responses to (1) pressure pain and (2) combined nonpainful visual, auditory, and tactile motor stimulation. The inventors then combined pain and multisensory brain measures to obtain a cross-validated signature for FM status.

Thus, one aspect of this disclosure is a method of detecting fibromyalgia (FM) in a subject by applying a stimulus to the subject and detecting brain activity of the subject in response to the stimulus using functional Magnetic Resonance Imaging (fMRI). The stimulus may be selected from at least one of a pressure pain stimulus, and a non-painful, multisensory stimulus. The multisensory stimulus preferably comprises visual, auditory, and tactile-motor stimulation. A brain map is generated that represents the brain activity of the subject in response to the stimulus. The brain map of the subject is compared to a neurologic signature map, which represents the brain activity indicative of FM in the subject. The subject may be diagnosed as having FM if the brain map from the subject in response to the stimulus is at least 70% identical to the neurologic signature map that is indicative of FM. In these methods, the subject may be diagnosed as having FM if the brain map from the subject in response to the stimulus is 70%, 80%, 90%, 95%, or 100% identical to the neurologic signature map that is indicative of FM. In these methods, the subject may be diagnosed as having FM if the brain map from the subject in response to the stimulus is any integer between 70 and 100% identical to the neurologic signature map that is indicative of FM. In these methods, the subject is preferably a human.

In these methods, the neurologic signature map may comprise an fMRI pattern created in a subject known to have FM in response to pain created by the application of pressure to a surface of the subject and that is at least 70% identical to the fMRI patterns shown in FIG. 1A. In such methods, the pressure applied to the subject may be about 4.5 kg/cm$^2$. This pressure may be applied to a limb of the subject, including for example a finger of the subject.

In these methods, the fMRI pattern may be created by detecting brain activity in the subject known to have FM in brain regions of major targets of ascending nociceptive afferents. Such brain regions may be selected from the group consisting of the thalamus, primary and secondary somatosensory regions (SI/SII), posterior, mid and anterior insula and adjacent opercula, midbrain, dorsal anterior cingulate cortex, inferior frontal gyms, amygdala, and combinations thereof. In these methods, the neurologic signature map may comprise an fMRI pattern created in a subject known to have FM in response to pain created by the application of pressure to a surface of the subject and that is at least 70% identical to the fMRI patterns shown in FIG. 2A. Similarly, in such methods, the pressure applied to the subject may be about 4.5 kg/cm², and this pressure may be applied to a limb of the subject, including for example a finger of the subject.

In these methods, the neurologic signature map may comprise an fMRI pattern created in a subject known to have FM in response to simultaneous presentation of visual, auditory, and tactile stimulation and that is at least 70% identical to the fMRI patterns shown in FIG. 3A. The simultaneous presentation of visual, auditory, and tactile stimulation may comprise the simultaneous presentation of full-field flashing light, a series of auditory tones presented at a temporal frequency, and repeated touching of the subject's fingers. In such methods, the brain map of the patient may be compiled based on activation patterns in brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof, during painful pressure and analyzed using linear support vector machines, and the neurological signature map is at least 70% identical to the FM-pain classification brain pattern shown in FIG. 2A.

In these methods, the brain map of the patient may be compiled based on whole-brain activation patterns during non-painful multisensory stimulation analyzed using linear support vector machines and the signature map is at least 70% identical to the FM-pain classification brain pattern shown in FIG. 3A.

In exemplary aspects of these methods, the brain map of the patient is compiled using logistic regression to combine each of a) an fMRI pattern created in the brain of the subject in response to pain created by the application of pressure to a surface of the subject; and b) an fMRI pattern created in the subject in brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof, during painful pressure and analyzed using linear support vector machines; and c) an fMRI pattern created in the brain of the subject in response to non-painful multisensory stimulation analyzed using linear support vector machines. Similarly, the neurologic signature map may be compiled using logistic regression to combine each of a) an fMRI pattern created in the brain of a subject known to have FM in response to pain created by the application of pressure to a surface of the subject; and b) an fMRI pattern created in a subject known to have FM in brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof, during painful pressure and analyzed using linear support vector machines; and c) an fMRI pattern created in the brain of a subject known to have FM in response to non-painful multisensory stimulation analyzed using linear support vector machines.

In these methods, the step of comparing the brain map and the neurologic signature map may comprise applying the neurologic signature map to the brain map of the subject to provide a response value.

Alternatively or additionally, the step of comparing the brain map and the neurologic signature map may comprise analyzing similarities and dissimilarities between portions of the brain map of the subject and the corresponding portions of the neurologic signature map.

In an exemplary aspect of these methods, the subject is diagnosed with FM when at least one brain map of the subject is at least 90% identical to the neurologic signature map.

In these methods, additional physical or neurological diagnostic information from the subject may be used in conjunction with the fMRI brain maps to aid in the diagnosis of FM in the subject. For example, the subject may be diagnosed with FM based on comparison of the brain map of the subject to the neurologic signature map and in conjunction with at least one of heart rate variability and fitness test results for the subject.

In another aspect, this disclosure provides a method of evaluating the efficacy of a putative treatment of fibromyalgia (FM) in a subject. In this method, a stimulus is applied to the subject and the brain activity of the subject in response to the stimulus is detected using fMRI, just as described above. A brain map is created and compared to a neurologic signature map just as described above. Thereafter, a putative therapeutic treatment for FM is administered to the subject. Unitive therapeutic treatment may comprise one or more pharmaceutical agents. Following the administration of the putative therapeutic treatment for FM to the subject, the subject is again subjected to a stimulus and the brain activity of the subject is recorded using fMRI in response to the stimulus, just as described above. A second brain map is produced and compared to a neurologic signature map just as described above. The putative therapeutic treatment of FM may be evaluated to be effective in the treatment of FM if the brain map created prior to administration of the putative treatment is more similar to the neurologic signature map than is the brain map created after the administration of the putative treatment. Alternatively, the putative therapeutic treatment of FM may be evaluated to be ineffective in the treatment of FM if the brain map created after administration of the putative treatment is more similar or identical to the neurologic signature map than is the brain map created before the administration of the putative treatment. In these methods, the similarity of the brain maps created before and after the administration of the putative therapeutic agent, to the neurologic signature map is evaluated by percent identity between the two maps, just as described above.

Another aspect of this disclosure provides a fibromyalgia (FM) evaluation system comprising a memory operable to store magnetic resonance imaging (MRI) data content; a processor in communication with the memory, the processor operable to: execute an analysis of stored data operable to: compare functional magnetic resonance image (fMRI) data content for two or more MRI data sets; determine data characteristics in one or more MRI data sets; and receive a criteria to sort the two or more MRI data sets, wherein the criteria comprises: 1) fMRI analysis of a subject receiving a pressure pain stimulus; 2) fMRI analysis of brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof in a subject receiving a pressure pain stimulus; and 3) fMRI analysis of a subject receiving non-painful, multisensory stimulus; and execute a user interface application in communication with the MIll data service, the user interface application operable to provide a first view of two or more thumbnails associated with each of the MIll data sets based on the data characteristic and the criteria, wherein the first view includes two or more thumbnails associated with the two or more MIll data sets.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become readily apparent from the Description of Embodiments, particularly when taken together with the drawings.

BRIEF DESCRIPTION OF DRAWINGS

FIG. 2A shows the support vector machine pattern of whole-brain voxel weights that optimizes classification of patients with FM and healthy participants. The voxel-by-voxel weights are provided for 3 representative regions (anterior SII, right dorsolateral, and dorsomedial prefrontal cortex) to illustrate the concept of weighted pattern. FIG. 2B shows the regions whose voxel weights contributed most reliably to the prediction of FM status ($q<0.05$ FDR corrected for the first 2 rows; P-uncorrected<0.001 to further illustrate the findings).

FIG. 3A shows the support vector machine pattern of whole-brain voxel weights that optimizes classification of patients with FM and healthy participants. The voxel-by-voxel weights are provided for 4 representative regions (visual cortex, auditory cortex, basal ganglia, and posterior cingulate) to illustrate the concept of weighted pattern. FIG. 3B shows regions whose voxel weights contributed most reliably to the prediction of FM status (FDR corrected). The top row matches the view of (FIG. 3A), showing that the most reliably predicting voxels correspond to those showing the highest and lowest weights. The last 3 rows represent sagittal, coronal, and axial views showing all predictive voxel clusters.

FIG. 4A shows the receiver-operating characteristic plot displaying sensitivity and specificity properties for the combined classifier. FIG. 4B (left panels) show the individual subjects' data in the join space of NPSp and multisensory or FM-pain and multisensory pattern responses. The shadowed areas represent 95% confidence regions for each group. The coefficients of correlation between pattern expression scores for healthy participants are: multisensory and NPSp, r=0.17 (P=0.92), multisensory and FM-pain, r=−0.26 (P=0.12), and NPSp and FM-pain, r=0.015 (P=0.93). In addition, for patients with FM: multisensory and NPSp, r=−0.24 (P=0.14), multisensory and FM-pain, r=−0.09 (P=0.59), and NPSp and FM-pain, r=0.39 (P=0.017). FIG. 4B (right panels) represent the group means (and SE) in the same spaces. Outlier tests were performed ($\geq 3.5$ SD from the mean of the subject's group). Only one control showed a value more similar to the fibromyalgia group than to the healthy control group (z=3.93) for the FM-pain pattern.

DESCRIPTION OF INVENTION

Described herein is a brain-based neurologic signature that serves as a diagnostic and evaluative marker of fibromyalgia (FM). As further described herein, these neurologic signatures are indicative of FM, discriminate FM from normal, healthy subjects, and may predict FM severity at the level of the individual person. The neurologic signature can be applied to individuals in the diagnosis and treatment of FM, as well as to compare efficacy of therapeutic treatments. Accordingly, further described herein are methods for detecting FM, diagnosing FM, and determining efficacy of a putative therapeutic treatment for FM using the neurologic signature.

Functional magnetic resonance imaging or functional MM (fMRI) is an imaging procedure that measures brain activity by detecting associated changes in blood flow. This technique relies on the fact that cerebral blood flow and neuronal activation are coupled. When an area of the brain is in use, blood flow to that region also increases. For example, blood oxygen-level dependent (BOLD) fMRI exploits the different magnetic signals generated by oxyhemoglobin and deoxyhemoglobin to identify areas of the brain with high oxygen demand, indicating increased activity. By generating a number of images in quick succession, changes in activity in response to a given stimulus can be detected, thereby demonstrating the correspondence between the stimulus and the brain region(s) involved in the task. BOLD fMRI is now routinely used to measure regional cerebral blood flow (rCBF) in response to changes in neuronal activity. While application of fMRI in the context of FM is plausible, until now no reliable fMRI application to detect FM has been developed that has been demonstrated to be both sensitive and specific to FM (or any subtype of pain) within an individual person, in a manner validated across different MRI scanners.

Figure 2A:
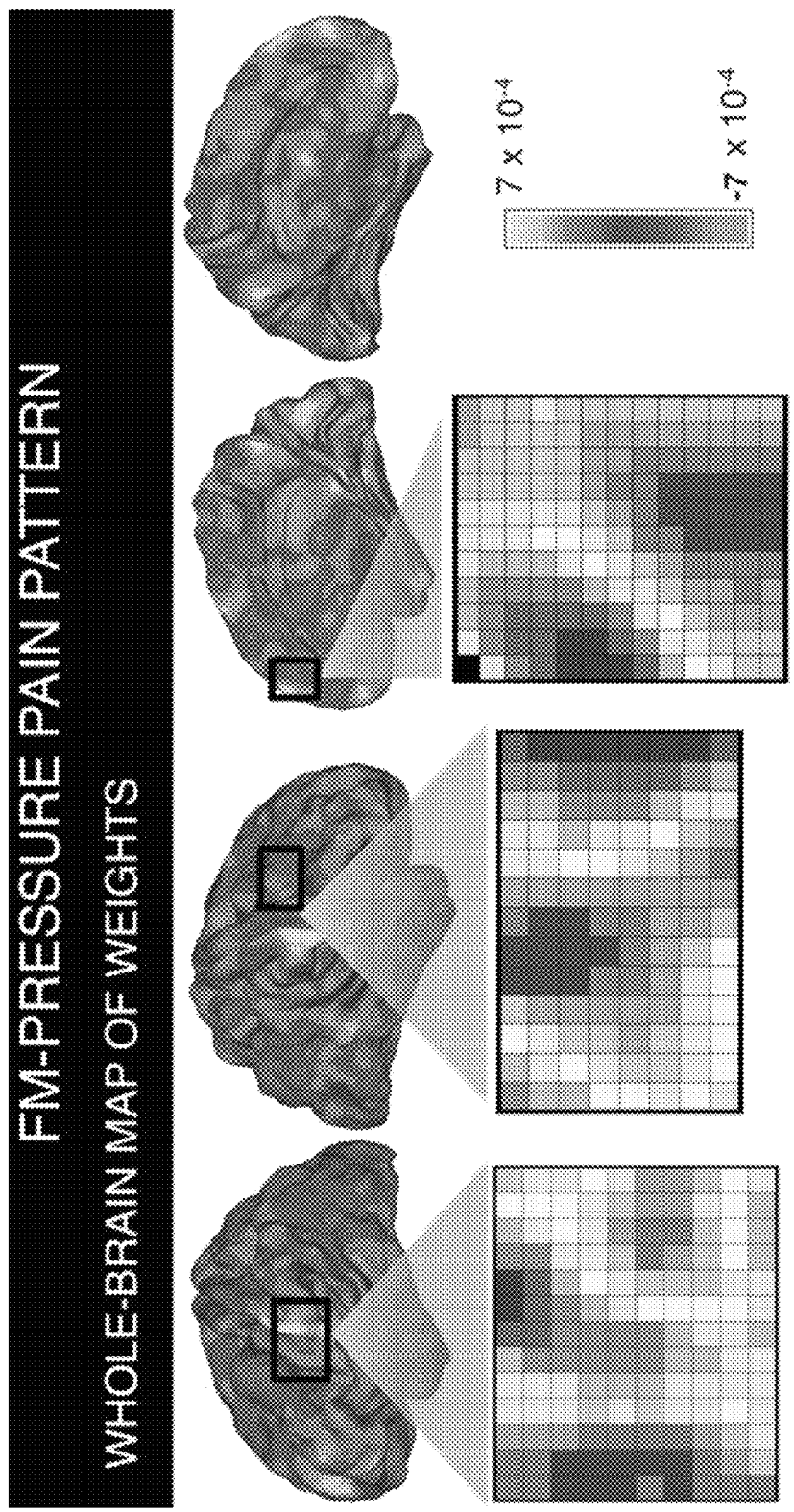
FIGS. 2A and 2B show multivariate brain pattern that predicts fibromyalgia (FM) status on the basis of brain activation during painful (pressure) stimulation. Positive weight values reflect higher pain-evoked activation in patients with FM relative to healthy participants, whereas negative weight values reflect reduced pain-evoked activation in patients with FM.
Figure 3A:
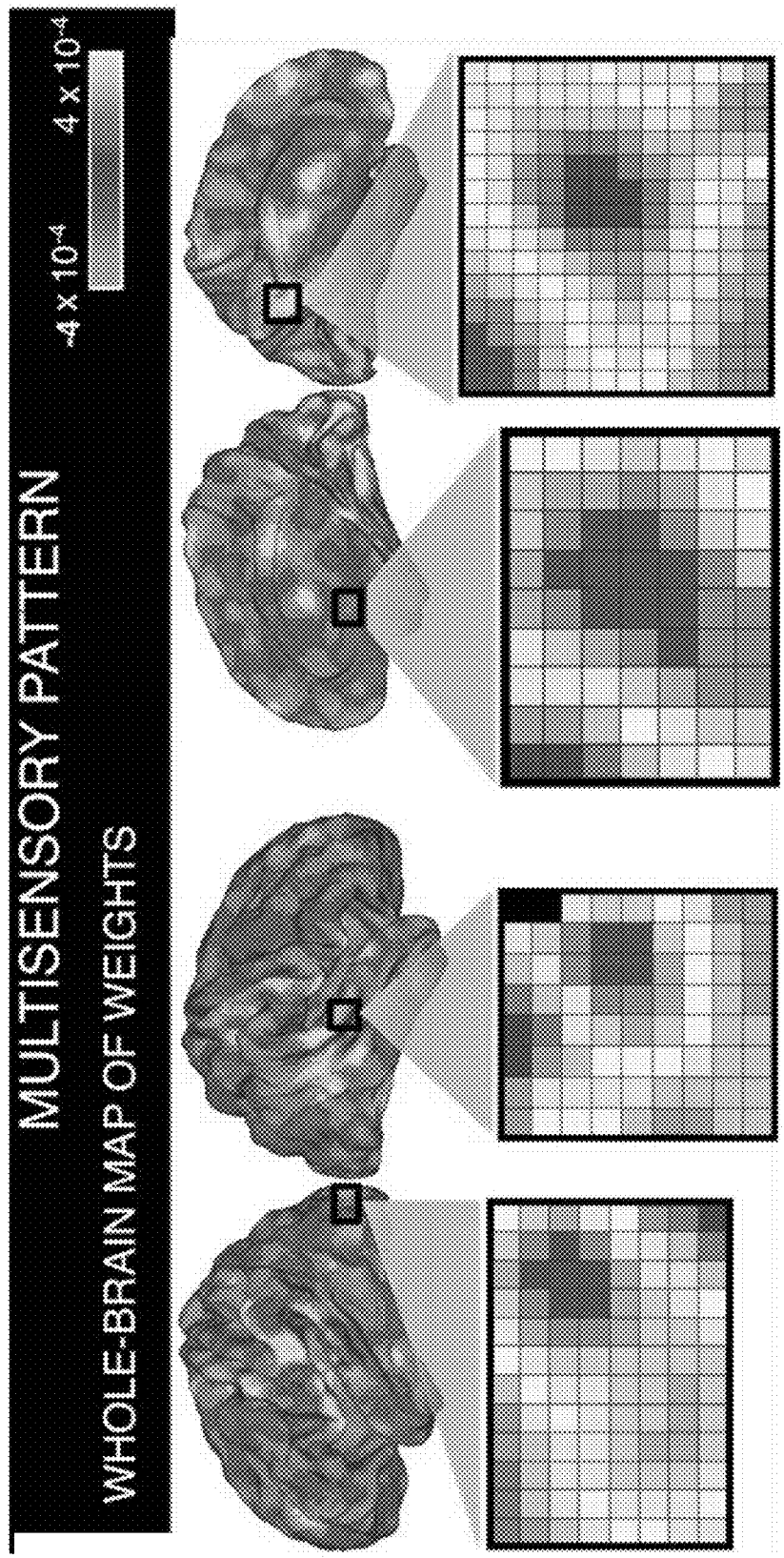
FIGS. 3A and 3B show multivariate brain pattern that predicts FM status on the basis of brain activation during multisensory stimulation. Positive weight values reflect higher multisensory-evoked activation in patients with FM relative to healthy participants, whereas negative weight values reflect reduced multisensory evoked activation in patients with FM.

The neurologic signature (also referred as a signature map or normative map or reference map), comprises an fMRI pattern that is indicative of FM in a subject. In one embodiment, the neurologic signature comprises an fMRI pattern that is least about 70% identical to the fMRI pattern shown in one of FIGS. 1A, 2A, and/or 3A. The identity may be in terms of overlapping brain voxels or shared variance. The term "voxel," as used herein, refers to a point or three-dimensional volume from which one or more measurements are made. A voxel may be a single measurement point, or may be part of a larger three-dimensional grid array that covers a volume. In various embodiments, the neurologic signature comprises an fMRI pattern that is at least about 65%, or at least about 70%, or at least about 75%, or at least about 80%, or at least about 85%, or at least about 90%, or at least about 95% identical, or at least about 96% identical, or at least about 97% identical, or at least about 98% identical, or at least about 99% identical (or any percent identity between 60% and 99%, in whole integer increments), to the fMRI pattern of FIGS. 1A, 2A, and/or 3A. In one embodiment, the neurologic signature comprises an fMRI pattern that is substantially identical to the fMRI pattern shown in FIG. 1A. In one embodiment, the neurologic signature comprises the fMRI pattern shown in FIG. 1A. In one embodiment, the neurologic signature comprises an fMRI pattern that is substantially identical to the fMRI pattern shown in FIG. 2A. In one embodiment, the neurologic signature comprises the fMRI pattern shown in FIG. 2A. In one embodiment, the neurologic signature comprises an fMRI pattern that is substantially identical to the fMRI pattern shown in FIG. 3A. In one embodiment, the neurologic signature comprises the fMRI pattern shown in FIG. 3A.

The development and validation of the neurologic signatures are described in detail in Examples 1-8. As described in Examples 2-8, fMRI analyses identified three neurologic signatures comprising a pattern of fMRI activity across brain regions, that was associated with FM in a subject and could diagnose FM and predict severity of FM at the level of the individual person. The pattern included brain regions including the major targets of ascending nociceptive afferents. These regions include the thalamus, primary and secondary somatosensory regions (SI/SII), posterior, mid and anterior insula and adjacent opercula, midbrain, dorsal anterior cingulate cortex (ACC), inferior frontal gyrus and amygdala.

One neurologic signature showed ≥92% sensitivity and ≥94% specificity in discriminating FM from healthy subjects.

The inventors used signal values from the voxels, in the a priori map to predict FM, using leave-two-subject-out cross-validation. The results were a spatial patterns of regression weights across brain regions, which were prospectively applied to fMRI activity maps obtained from new participants. Application of the signature to an activity map (e.g., a map obtained during sensory stimulation) yielded a scalar response value.

In another embodiment, a method of detecting FM in a subject uses the neurologic signatures of this disclosure. The method comprises applying a stimulus to the subject and measuring the brain or neuronal activity in the subject in response to the stimulus by fMRI to generate a brain map of the subject, which brain map is compared to a neurologic signature map from a subject known to have FM.

It is noted that although the signature maps were developed in response to an experimental stimulus (e.g., physical pain stimulus or non-painful sensory stimulus), it is believed that the maps are applicable to pain induced by a variety of stimuli and are useful to predict FM in response to a variety of stimuli. Accordingly, the subject may be given any sensory stimulus to induce pain or unpleasant sensations. Examples of stimuli include without limitation, thermal (heat or cold), mechanical (such as a touch or a pinprick), electrical, ischemic, tissue injury, or administration of a compound (chemical).

The brain map of the subject (or subject map) comprising an fMRI pattern induced in the subject in the response to the stimulus is then compared to the neurologic signature maps of the present invention. In some embodiments, the term "comparing" comprises applying the neurologic signature to the brain activity map of the subject to produce a signature response value.

In some embodiments, the term "comparing" means evaluating the brain activity in a particular region or voxel of the subject map to the corresponding region or voxel in the signature map in order to identify similarities or dissimilarities between the fMRI patterns of the two maps.

In some embodiments, the connectivity values among brain regions specified in the subject's brain map are compared with the connectivity values in the signature map. "Connectivity" is a known term in the field of human neuroimaging, and refers to the assessment of the strength or pattern of statistical relationships among regions. In some embodiments, it refers to the strength of relationships among regions specified in the brain map (or portions of it), as summarized by metrics such as Pearson's correlation coefficients among regions, nonparametric correlations such as Kendall's Tau, Kruskal's Gamma, Spearman's Rho, and similar metrics; graph theoretic measures including Centrality, Path Length, Small-worldness, and similar measures of global connectivity; or other measures of similarity or dissimilarity in functional relationships.

Connectivity may reflect functional connectivity, defined here as the relationship between activity measures in two or more regions over time assessed with fMRI, Positron Emission Tomography, Arterial Spin Labeling fMRI, or related methods; or structural connectivity, defined here as measures related to the integrity of white-matter (axonal) tracts connecting two or more regions defined by the neurologic signature pattern, as assessed using diffusion-weighted imaging, including diffusion-tensor imaging, diffusion-spectrum imaging, high angle resolution diffusion imaging, or similar techniques. The present invention includes methods comparing connectivity measures among brain regions defined by all or part of the neurologic signature pattern, either quantitatively by comparing samples from an individual person of interest to other normative connectivity samples, or by qualitative assessment (i.e., by a physician).

The comparison and analyses of the subject's fMRI data may be performed by a computer to provide an output. In some embodiments, such output may be a single numeric value or it may be a series of numeric values. The comparison and analyses of the fMRI data may also be performed by an individual, such as a physician. Analysis of fMRI data may be performed using standard statistical methods. Methods for statistical analyses of comparison of fMRI patterns are well known in the art and are incorporated herein. A number of computer programs based on pattern recognition or machine learning methods for the analysis of fMRI data are well known in the art and are commercially available (e.g. MATLAB Medical image Analysis) and may be used in methods of the present invention.

The analysis and determination of similarity and/or the dissimilarity between the signature map and the subject map yields information that may be used as the basis for diagnosis of FM and treatments. For example, the subject map may comprise an fMRI pattern that is identical or substantially similar to the signature pattern indicating the presence of FM in the subject but may vary in terms of the intensity or the magnitude of the signature, providing a measure of quantification of FM in the subject or the severity of FM experienced by the subject. In some instances, the subject's brain map may comprise an fMRI pattern that is dissimilar from the signature map in that the subject map may comprise a pattern that shows different levels of brain activity in different portions of the map as compared to the corresponding portions of the signature map. In some instances, the subject map may comprise a pattern that exhibits different relationships among the activity levels in one or more portions of the subject map, or "connectivity," as compared to the corresponding portions in the signature map.

Thus, these methods may comprise applying the signature map to the subject map to provide a scalar response value. The scalar response value is a numerical value that reflects the magnitude of the fMRI signature in the subject and provides a means of quantifying FM in the subject. For example, a higher scalar response value would indicate a greater severity of FM in the subject and a lower scalar response value may indicate a lower severity of FM in the subject. In some embodiments, these methods further comprise quantifying the severity of FM in the subject based on the response value.

A number of brain regions have been implicated in FM and based on the knowledge in the art, one skilled in the art will be able to interpret the results of the comparison between the subject map and the signature map, or use quantitative metrics from normative populations to serve as distribution against which anomalous neurophysiological features related to FM may be detected.

These methods may also further comprise administering a therapeutic treatment or a putative therapeutic treatment of FM to the subject. The term therapeutic treatment means a regimen intended to have a preventive, ameliorative, curative, or stabilizing effect. Examples of therapeutic treatment include pharmaceutical agents such as analgesics, physical treatment (e.g., massage or acupuncture), electrical treatment, thermal treatment, electromagnetic radiation, counseling, or a surgical, medical, or dental procedure. The term "analgesics" includes any drug that is used to achieve relief from pain, and includes without limitation, organic compounds, inorganic compounds, peptides or proteins, and nucleic acids. The type and the dosage of the therapeutic treatment to be administered may be selected on the basis of the comparison of the subject map and the signature map.

In some embodiments, the method further comprises measuring another indicator of FM. Such indicators may be physical assessments of the subject including for example heart rate variability performance in specific fitness tests.

Another aspect is a method to rule out FM in a subject comprising measuring brain activity by fMRI in a subject to generate a brain map of the subject and comparing the brain map of the subject to the signature maps of this disclosure to identify any dissimilarities between the structural and functional connectivity of the brain regions of the subject. In this embodiment, the subject's data reflects brain activity of the subject in the resting state or any other state whose purpose of assessment is to quantify structural or functional connectivity among brain regions. 'Connectivity' is an established general method in the field of human neuroimaging, and refers to the assessment of the strength or pattern of statistical relationships among regions. Here, it refers to the strength of relationships among regions specified in the neurologic signature map or part of the map, as summarized by metrics such as Pearson's correlation coefficients among regions, nonparametric correlations such as Kendall's Tau, Kruskal's Gamma, Spearman's Rho, and similar metrics; graph theoretic measures including Centrality, Path Length, Small-worldness, and similar measures of global connectivity; or other measures of similarity or dissimilarity in functional relationships.

Connectivity may reflect functional connectivity, defined here as the relationship between activity measures in two or more regions over time assessed with fMRI, Positron Emission Tomography, Arterial Spin Labeling fMRI, or related methods; or structural connectivity, defined here as measures related to the integrity of white-matter (axonal) tracts connecting two or more regions defined by the neurologic signature pattern, as assessed using diffusion-weighted imaging, including diffusion-tensor imaging, diffusion-spectrum imaging, high angle resolution diffusion imaging, or similar techniques. The present invention applies to methods comparing connectivity measures among regions defined by all or part of the neurologic signature pattern, either quantitatively by comparing samples from an individual person of interest to other normative connectivity samples, or by qualitative assessment (i.e., by a physician).

In another embodiment, the present invention includes a method for determining efficacy of a therapeutic treatment or a putative therapeutic treatment. The method comprises administering a therapeutic treatment to a subject, applying a stimulus to the subject and measuring brain activity of the subject in response to the stimulus to generate a brain map of the subject. The stimulus may be provided before, after or simultaneously with the administration of the treatment. The method further comprises comparing the brain map of the subject with the signature maps of this disclosure to identify similarities or dissimilarities between the two as discussed above. For example, a lower scalar response value upon administration of the treatment would be indicative of the efficacy of the treatment. The subject map may be further compared with a control subject map obtained from the same subject or another subject treated with placebo or treated with a therapeutic treatment with known efficacy.

The neurologic pattern and neuron activation in the brain of a FM patient with pain is different from that of healthy persons with similar painful stimuli. FM patients have an increased pain sensitivity, hyperalgesia and frequently also a central augmentation of pain. For example, a patient with FM who receives a painful stimulus applied to his/her thumbnail will have an fMRI that differs from that for the healthy control group when the same pain stimulus is applied. Differences in the brain regions and pattern of neuron activation between the two sets of fMRIs can be objectively observed. The FM pain patient will exhibit extensive common patterns of neuron activation of pain in related cortical areas.

Conversely, the intensity needed to observe a common pain level on the fMRI will be less for the FM patient than for the healthy subjects.

The actual evaluation whether a given person is suffering from FM is conducted in an fMRI machine by initially placing the patient in a comfortable position within the bore of the magnet of the machine. The patient's head is immobilized, for example with a vacuum bean bag, a foam headrest and a removable plastic bar across the bridge of the nose, although if there is concern about a tremor or movement, a bite bar can be used instead to hold the head steady, and a pain stimulus is applied while the patient's brain is scanned at and an fMRI image of the brain activity is taken. To avoid the effect of sensitization, the pain stimulus is applied in a random order. The modality of the stimulus will also be random.

Members of the control group were previously subjected to the same physical pain stimulus or multisensory stimulus at intervals, initially up to a sensation threshold level. For example, for painful stimulus, the sensation threshold level lies just below the pain threshold level, and thereafter to the pain threshold level and, finally, to the maximum tolerable pain level. The subjects' brains are scanned and fMRI images thereof are taken. The fMRI images of the members of the control group are statistically combined into a standard fMRI image or chart of the average brain activities of the members of the group. The standard chart is then stored, for example in a computer memory or other suitable memory or storage device.

The same protocol used for the control group is used on the FM patient by preferably applying the pain and or multisensory stimulus to the painful body part and the contralateral body part. It should be noted, however, that for purposes of the present disclosure the pain stimulus may be applied to parts of the body not affected with chronic pain in order to generate fMRI images that reflect the presence or absence of chronic pain.

The present invention also relates to systems that may be used in combination with performing the various methods according to the present invention. These systems may include a brain activity measurement apparatus, such as a magnetic resonance imaging scanner, one or more processors and software according to the present invention. These systems may also include means to present information to a device operator during testing, or upon completion of testing, or at a later time. These systems may also include software for automated diagnosis of the subject, or testing of brain activation metrics. These systems may also include mechanisms for communicating information such as instructions, stimulus information, physiological measurement related information, and/or subject performance related information to the subject or an operator. Such communication mechanisms may include a display, preferably a display adapted to be viewable by the subject while brain activity measurements are being taken. The communication mechanisms may also include mechanisms for delivering audio, tactile, temperature, or proprioceptive information to the subject. In some instances, the systems further include a mechanism by which the subject may input information to the system, preferably while brain activity measurements are being taken.

The present invention also relates to software that is designed to perform one or more operations employed in combination with the methods of the present invention. The various operations that are or may be performed by software will be understood by one of ordinary skill, in view of the teaching provided herein.

In another embodiment, computer assisted method is provided comprising: measuring activity of one or more internal voxels of a brain; employing computer executable logic that takes the measured brain activity and determines an estimate of a condition of the subject computed from the measured activity; and communicating information based on the determinations to the subject or device operator.

This disclosure is further illustrated by the following examples which should not be construed as limiting. The examples are illustrative only, and are not intended to limit in any manner any of the aspects described herein.

EXAMPLES

The following materials and methods were used in conducting the experiments described in the following examples.

Subjects studied: Seventy-two subjects participated, including 37 female patients with FM (1990 American College of Rheumatology criteria for FM) and 35 female matched healthy controls. Patients and healthy subjects were matched for age, education status, and handedness (all right handed). The patients were consecutively recruited during clinical follow-up in the rheumatology service (CIMA, Barcelona) to provide a homogeneous sample with severe and persistent FM symptoms. Vision and hearing were normal upon neurological examination for all patients and healthy participants.

|  | Patients with FM (N = 37) | Healthy participants (N = 35) | Statistics |
| --- | --- | --- | --- |
| Age (mean ± SD) | 46.27 ± 7.72 | 43.86 ± 6.05 | t = 1.47, P = 0.15 |
| Education (y) | 14.19 ± 4.47 | 15.09 ± 4.90 | t = 0.81, P = 0.42 |
| Illness duration (mo) | 80.41 ± 52.05 |  |  |
| Tender points (number) | 15.92 ± 1.96 |  |  |
| FIQ (total score) | 66.86 ± 15.79 |  |  |

-continued

|  | Patients with FM (N = 37) | Healthy participants (N = 35) | Statistics |
|---|---|---|---|
| FIQ (functional capacity) | 4.81 ± 1.84 | | |
| SF-36 (perception of health) | 30.33 ± 17.63 | | |
| HADS (depression) | 8.89 ± 4.72 | | |
| HADS (anxiety) | 11.54 ± 4.15 | | |
| Clinical pain (0-100 NRS) | 72.03 ± 14.82 | | |

| Antidepressants | Number of patients with FM (N = 37) |
|---|---|
| SSRI | 15 |
| NS-SSRI | 3 |
| SNRI | 6 |
| NaSSAs | 1 |
| TCA and SSRI | 3 |
| Anxiolytics | |
| Benzodiazepines | 18 |
| Hypnotics-Benzodiazepinics, long half-life | 1 |
| medium half-life | 1 |
| short half-life | 3 |
| Gabapentin | 10 |
| Analgesic drugs | 33 occasionally (11 stably) |
| Non-opioid (ibuprofen and paracetamol) | 11 |
| Opiod (tramadol) | 6 |

All subjects were right handed; The total number of patients receiving antidepressant medication was 28. Analgesic drugs include ibuprofen, paracetamol, and tramadol. Patients were asked to refrain from taking nonstable (rescue) nonsteroidal anti-inflammatory drug/analgesic drugs (i.e., ibuprofen, paracetamol, and tramadol) 72 hours before magnetic resonance imaging assessment. The number in parenthesis corresponds to subjects taking the analgesic medications under a stable regime. FIQ, Fibromyalgia Impact Questionnaire; FM, fibromyalgia; HADS, Hospital Anxiety and Depression Scale; NaSSAs, noradrenergic and specific serotonergic antidepressants; NRS, numerical rating scale; NS-SSRI, non-selective serotonin reuptake inhibitor; SF-36, 36-Item Short-Form Health Survey; SNRI, serotonin-norepinephrine reuptake inhibitor; SSRI, selective serotonin reuptake inhibitor; TCA, tricyclic antidepressant.

We administered the following scales in a visit before the magnetic resonance imaging (MRI) appointment: Fibromyalgia Impact Questionnaire (FIQ); the 36-Item Short-Form Health Survey, General Perception of Health; the Hospital Anxiety and Depression Scale (HADS). Patients were allowed to continue with their stable medical treatment, as listed in the table, but were asked to refrain from taking occasional rescue analgesic drugs (ie, nonsteroidal anti-inflammatory drugs, paracetamol, and tramadol) 72 hours before scanning session. Control subjects with relevant medical and neurological disorders, any form of chronic or acute pain, substance abuse, or history of psychiatric illness were not considered for inclusion. Contraindication to MRI, including pregnancy, was a general exclusion criterion for both groups. Clinical pain in deep tissue was assessed using a 101-point verbal scale. A score of 0 expressed no pain and a score of 100 the most intense pain imaginable, perceived in the body as a whole, or in most of its extension, rather than referring to any focal tenderness. Patients were asked to report spontaneous pain approximately 1 hour before the scanning session. All healthy participants rated "0" for this measure.

Description of functional magnetic resonance imaging tasks and stimuli used Multisensory task: A block-design functional MRI (fMRI) paradigm was used, with alternating 30-second periods of rest (no stimulation) and activation (concurrent visual, auditory, and tactile-motor stimulation), completing a total of 4 rest-stimulation cycles. A subset of these data (from 25 controls and 35 patients) was used in a previous publication by our group. The multisensory stimuli consisted of the simultaneous presentation of visual (3 Hz, equivalent to 6 color reversals per second) full-field flashing checkerboard composed of a grid of black and white alternating squares (80±10 lux) and auditory stimulation (series of 15 tones of frequencies comprised in the range of 233.1-1318.5 Hz, presented at a temporal frequency of 3 Hz, with an intensity of 75±5 dB) and a finger-opposition task during which subjects were instructed to touch the tip of their right thumb with the other fingers (from index to little finger). In our multisensory assessment, we were interested in a more naturalistic presentation of sensory stimuli (and motor response) that are usually combined in daily life rather than in modality-specific alterations. As a first approach, this allowed us to maximize signal power and challenge both sensory and motor systems efficiently.

Low- and High-Pressure (Healthy Participants Only) Stimulation Tasks

Pressure stimulation tasks involved a block design fMRI paradigm consisting of 3 conditions per stimulation cycle repeated 5 times. Each cycle began with a rest condition with pseudorandom duration (range: 20-32 seconds), followed by a brief auditory stimulus (600-millisecond tone), followed by a 6-second anticipatory period, and then a 10-second pressure pain period. Each subject was asked to rate pain intensity and unpleasantness immediately after the end of the fMRI scanning sequence (run) using a numerical rating scale (NRS) ranging from 0 (not at all painful/unpleasant) to 100 (worst pain imaginable/most unpleasant imaginable). All participants completed a low-pressure pain task first, with pressure set at 4.5 kg/cm2. Approximately 10 minutes later, 28 healthy participants (out of 35) completed a second, high-pressure pain task, with stimulus intensity individualized based on the calibration session to reliably provoke severe but tolerable pain (5.90±0.62 kg/cm2), comparable to the experience of patients with FM at 4.5 kg/cm2. As in previous studies, pressure pain stimuli were delivered using a hydraulic device capable of transmitting controlled pressure to 1-cm2 surface placed on the subjects' right thumbnail. In a calibration session, each subject was trained to report pain intensity and unpleasantness to different pressure stimuli ranging from 2 to 9 kg/cm2 (or up to tolerance threshold) using the NRS described above. A stimulus of 4.5 kg/cm2 was selected to reliably provoke intense pain (above 60 in the NRS but tolerable) in the patient group. This stimulus is only slightly more intense than what was used to determine tender points during clinical assessment in patients (4 kg/cm2). The 10-second 4.5 kg/cm2 was able to evoke, during the calibration assessment, a mean pain intensity of 73.15±19.76 points in the patient group and a 36.47±20.38 points in the healthy control group (between-group effect: t=7.75, P<0.0005). For healthy participants, we also determined the minimum pressure intensity that was required during the calibration session to provoke severe (above 60 in the NRS) but tolerable pain (5.90±0.62 kg/cm2).

Statistical Analyses

Behavioral analyses: Two-sample t tests (for post-scan pain intensity and unpleasantness) were computed in SPSS (IBM SPSS Statistics for Macintosh, Version 20.0).

Magnetic resonance imaging acquisition and preprocessing: We scanned participants on a Philips Achieva 3.0 TX system (Philips Healthcare, Best, The Netherlands), with an 8-channel phased-array head coil and single-shot echo planar imaging. Each functional sequence consisted of gradient recalled acquisition in the steady state (repetition time [TR]=2.000 milliseconds; echo time=35 milliseconds; flip angle=90°; dummy volumes=4) within a field of view of 23 cm, a 96×69-pixel matrix, and slice thickness of 4 mm (interslice gap, 1 mm). Twenty-two slices parallel to the anteroposterior commissure provided whole-brain coverage. Imaging data were processed using MATLAB (v2011b; The MathWorks Inc, Natick, Mass.) and Statistical Parametric Mapping software (SPM8; The Wellcome Department of Imaging Neuroscience, London). Preprocessing involved motion correction, spatial normalization, and smoothing using a Gaussian filter (fullwidth half-maximum, 8 mm). Data were normalized to the standard SPM echo planar imaging template provided by SPM8 and resliced to 2 mm isotropic resolution in Montreal Neurological Institute space. Regarding motion correction, translation and rotation estimates (x, y, z) were <2 mm or 2°, respectively, for all the participants, and no subjects were excluded because of artifacts or head displacement/rotations. To address the potential effects of head motion on the FM status prediction results, we computed a single motion index per subject for each fMRI task (see full description of the method in Pujol J, et al., Neuroimage (2014) 101:87-95; see also Power J D, et al., Neuroimage (2012) 59:2142-54). Briefly, we computed a measure for mean interframe motion due to translation (x, y, z), $mIM_{tr}$, and a measure for mean interframe motion due to rotation (pitch, yaw, roll), $mIM_{rot}$. Although $mIM_{tr}$ is a distance, $mIM_{rot}$ is an angle. The combined measurement was based on an average of both=$(mIM_{tr}+r\times mIM_{rot})/2$, where r is the approximate average distance of all brain voxels to the rotation principal axis. The multiplicative factor r is necessary to transform the angle $mIM_{rot}$ to its corresponding distance arc. Following previous authors, we set r=50 mm. Specific details about the computation of $mIM_{tr}$ and $mIM_{rot}$ are provided in Pujol J, et al., Neuroimage (2014); Supplementary Information file available at links.1ww.com/PAIN/A340). We did not observe between-group differences in motion during the multisensory paradigm (t=−0.28, P=0.78). However, for the pressure pain task, significant differences were observed in TR-by-TR head motion between patients with FM and healthy participants (patients. controls, t=2.49, P=0.02) (also between healthy subjects at the high and low-pressure intensities, t=2.38, P=0.02), whereas no differences emerged between patients and healthy participants when pain was matched (t=0.27, P=0.79). Importantly, the magnitude of the between-group difference in head motion was minimal (95% confidence interval for the head motion difference between patients and healthy participants: 0.01-0.16 mm). To account for the potential influence of head motion in the prediction model of FM status (see below, logistic multiple regression), we added the single subject measures of head motion for each task (pain and multisensory, for the sake of completeness) as independent variables in the model and verified that neither contributed significant variance to explaining the FM status (multisensory task: t=−0.84, P=0.40; pain task: t=0.20, P=0.84). To test whether motion parameters (during the pain task) were sufficiently informative to correctly classify patients from healthy participants, we used support vector machines (SVMs) with 6 motion regressors per subject as the classification features and the subjects' category (patient vs healthy participant) as the outcome. The results were not significant (cross-validated accuracy: 60%±5.7% [SE], P=0.10). We also checked and confirmed that the time course of the "nociception-positive NPS" response (see below) on a TR-by-TR basis was not correlated with motion parameter estimates, for any regressor for any subject (all P values>0.1). First-level single-subject models for functional magnetic resonance imaging data: We used a conventional general lineal model approach as implemented in SPM8 software to estimate brain responses to (1) multisensory stimulation and (2) pressure stimulation for each subject. For the multisensory task, a primary task regressor was created by convolving the sensory stimulation blocks with a canonical hemodynamic response function. The "off" (rest) condition served as an implicit task baseline. Parameter estimates were calculated at each voxel using the general linear model. A high-pass filter was used to remove low-frequency signal fluctuations ($1/128$ Hz). (Multisensory stimulation 2 baseline) contrast images for each participant were calculated. For the pressure stimulation task, signal response was modeled using separate regressors for the anticipatory and the pain periods, with a hemodynamic delay of 4 seconds. In 3 previous studies using similar procedures, we systematically observed that the duration of brain responses to 10-second pressure stimuli of similar intensities extends to 16 seconds (average response duration across pain processing regions), which is consistent with observations by different research groups. To account for this, pain-related activation was modeled using a pain condition of 16-second duration. A high-pass filter was used to remove low-frequency signal fluctuations ($1/128$ Hz). In agreement with our previous work, we did not model autocorrelations. Modeling autocorrelations has the potential disadvantage of producing biased parameter estimates when the autoregressive (AR) model assumptions are violated, which can result in reduced efficiency. Of note, models that do not consider autocorrelation have shown to generate unbiased parameter estimates (beta values, which we use here for classification purposes), even if the data are auto-correlated. (Pressure stimulation 2 baseline) contrast images for each participant were calculated. We studied brain response alterations during pain processing in patients with FM using 2 complementary approaches: (1) As a first test of pain-related brain responses, we applied the NPS brain signature, a multivariate fMRI-based brain pattern that was validated to specifically predict experimental pain (and not other unpleasant/arousing emotional experiences) in humans. The goal of this approach was to use a defined marker or process that has been well characterized in healthy individuals to test for abnormalities in the patient population. An advantage is that the NPS was trained to track pain intensity in a fine-grained way across multiple levels of stimulus intensity and was tested for specificity to pain and generalizability across a number of independent studies. (2) Because the NPS may not be sufficient to capture all pain-related differences between patients and controls, a second approach was to train a classifier optimized to discriminate patients with FM from controls. This pattern identifies pain-related signals that may be missed by the NPS. This second approach was also applied to the multisensory task (see below).

Computing Neurologic Pain Signature responses: We computed for each subject (patient with FM or healthy participant) a single scalar value representing their expression of the NPS pattern in response to pressure pain (using the contrast [pressure stimulation 2 baseline] images, as detailed below). For this analysis, we separated NPS regions likely to be related to nociceptive pain (associated with pain-evoked activation in the NPS) from those that play other modulatory roles (associated with pain-evoked deactivation in the NPS). In most of the regions in the NPS, pain is associated with increased overall activity. Such regions include the major targets of ascending nociceptive afferents, including the thalamus, primary and secondary somatosensory regions (SI/SII), posterior, mid and anterior insula and adjacent opercula, midbrain, dorsal anterior cingulate cortex (ACC), inferior frontal gyms and amygdala. We refer to pattern responses in this set of regions as the "nociception-positive NPS" (NPSp). In a subset of other medial regions, including the perigenual ACC (pgACC) and the posterior cingulate (PCC)/precuneus/paracentral lobule, pain was associated with deactivation in the original NPS pattern. These regions are not strongly linked to nociception and are not direct targets of nociceptive afferents, rather they have been associated with a variety of affective, autonomic, social, self referential, and decision-making functions. We refer to responses in this set of regions as the "nociception-negative NPS" (NPSn) and analyze this pattern separately from the NPSp due to its differential functional characteristics and considering the particular role of these regions, mostly the pgACC, in chronic pain. Of note, the local pattern of voxel weights is exactly the same as in the original NPS within the 2 NPS components (NPSp and NPSn).

Mediation analysis: We tested 2 separate mediation models to assess whether the relationship between FM status (FM vs healthy) and pain ratings during the fMRI pain task (intensity—model 1 and unpleasantness—model 2) were significantly mediated by NPS brain responses. The mediation analysis tested several joint hypotheses: Path a tested whether FM status (FM vs healthy) predicts NPSp responses. Path b tested whether NPSp responses predict subjective ratings of intensity (or unpleasantness), controlling for FM status. Finally, the Path a×b tested the mediation effect, i.e., whether NPSp responses during pressure pain explain a significant proportion of the covariation between FM status and subjective pain ratings. The analyses were conducted using the mediation toolbox that has been used and described extensively in a previous work (Wager T D, et al., Neuron (2008) 59:1037-50) with bias-corrected, accelerated bootstrap tests.

Multivariate pattern-based classification of patients with fibromyalgia vs healthy controls: We performed 2 analyses using linear SVMs to discriminate patients with FM and controls based on whole-brain activation patterns. The first analysis used activation patterns during painful pressure at 4.5 kg/cm2 pressure stimulation (FM-pain) and the second analysis used activations during non-painful multisensory stimulation (multisensory). The SVM was implemented in the Spider Toolbox (people.kyb.tuebingen.mpg.de/spider). It identifies a hyperplane (direction in multidimensional voxel space) that separates the 2 groups. Distances from the hyperplane are related to the likelihood a participant belongs to the patient vs control class and were used in the logistic regression analysis below. The FM-pain classifier was based on the (pressure stimulation-baseline) contrast, and the multisensory classifier was based on the (multisensory stimulation-baseline) contrast. In each analysis, we used leave-2-subject-out cross-validation, which ensured that the patterns we identified were always tested on new, out-of-sample individuals. Accuracy (sensitivity and specificity) was based on the cross-validation, and the final weight map was based on the full sample and was thresholded using a bootstrap test (q<0.05 false discovery rate (FDR)-corrected).

Logistic multiple regression to develop a combined classifier for fibromyalgia status: We used logistic regression to combine results from the 3 fMRI based classifiers (NPS, FM-pain, and multisensory) into a single signature of FM status. The predictors in the regression were: (1) the NPSp response, (2) the NPSn response, (3) the cross-validated FM-pain signature response (distance from the hyperplane), and (4) the cross-validated multisensory signature response. Logistic regression results were used to calculate sensitivity, specificity, and the area under the receiver operating characteristic curve. We assessed these values for each fMRI-based classifier (NPSp, FM-pain, and multisensory) independently and for the combined model.

Multivariate brain pattern responses and medication status: To examine the relationship between medication status and brain pattern responses, we performed a series of 2-sample t tests to compare between-group differences in pattern response between medicated and nonmedicated patients.

Multivariate brain pattern responses and clinical severity: We also tested whether the multivariate fMRI patterns used to classify FM status were correlated with clinical symptom severity. We performed linear regression (stepwise procedure in SPSS), including the 4 brain-derived (cross-validated) pattern response values as predictors (NPSp, NPSn, FM-pain, and multisensory) and each of the clinical measures as the dependent variable in 1 of 3 regression models (clinical pain, FIQ, and HADS depression scores). We included a fourth predictor representing the presence or absence of anxiolytic or antidepressant medication in each model, considering the significant correlation between NPS responses and antidepressant and anxiolytic medication status (further described in the Results section). For completeness, we also assessed zero-order Pearson correlations between brain measures and clinical symptom severity in patients with FM.

Example 1

Enhanced Pressure Pain Sensitivity in Patients with Fibromyalgia

In response to the low-pressure intensity fMRI task (4.5 kg/cm2), patients with FM (vs healthy participants) reported increased pain intensity (mean±SD, 71.71±14.47 for patients with FM, 48.48±18.31 for healthy participants; between-group effect: t 5=5.95; P<0.0005) and unpleasantness (68.24±18.84 for patients with FM, 44.11±19.98 for healthy subjects; between-group effect: t=5.24, P<0.0005). In the high-pressure intensity task (approx. 6 kg/cm2±0.62), healthy subjects reported equivalent pain levels as patients with FM stimulated at low pressure (t=0.61, P=0.54 for intensity and t=0.54, P=0.59 for unpleasantness).

Example 2

Figure 1A:
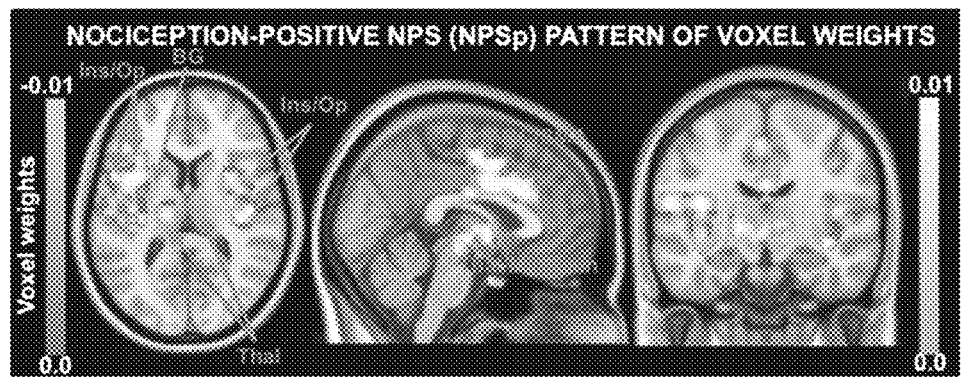
FIGS. 1A-1E show nociception-positive neurologic pain signature (NPS) (NPSp) map of voxel weights (FIG. 1A); pattern response per group (FIG. 1B); and contiguous regions (FIG. 1C). Error bars represent standard errors of the mean. ***$P<0.0001$. Responses to low-intensity stimulation in (FIG. 1B) were $21.87 \pm 14.00$ (t=9.5, $P<0.0001$) in patients with FM and $13.21 \pm 8.02$ in healthy participants (t=9.74, $P<0.0001$). Responses to high-intensity stimulation were $21.62 \pm 13.31$ in healthy participants (t=9.74, $P<0.0001$). NPSp pattern response significantly mediates (partial mediation) the relationship between clinical category (FM diagnosis present vs absent) and pain intensity (FIG. 1D), and pain unpleasantness (FIG. 1E) ratings in response to 4.5 kg/cm2 painful pressure. All coefficients in the mediation models have been tested for significance using 10,000 bootstrap tests. One-tail P-values are reported based on a directional a priori hypotheses (patients with FM will show greater NPS responses; and the greater the NPS response, the higher the pain ratings). ant, anterior; BG, basal ganglia; coeff, coefficient; dACC/SMA, dorsal anterior cingulate cortex and supplementary motor area; fMRI, functional magnetic resonance imaging; Ins, insula; L, left; Midbr, midbrain; Op, operculum; post, posterior; R, right; Thal, thalamus.
Figure 1B:
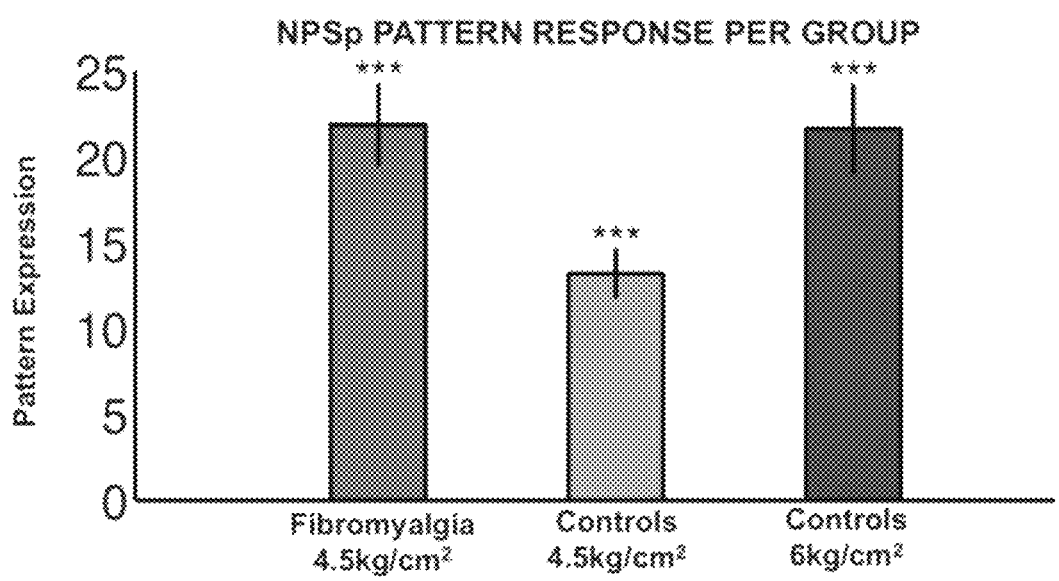

Neurologic Pain Signature Responses in Patients with Fibromyalgia Vs Healthy Controls FIG. 1A shows the NPSp pattern. Patients with FM and healthy subjects (at both stimulation intensities) showed significant NPSp responses, shown in FIB. 1B. Responses to the low-pressure fixed intensity (4.5 kg/cm2) were greater for patients with FM than for healthy participants (t 5 3.24; P 5 0.002), consistent with hypersensitivity to mechanical pain in FM. When subjective pain was matched between groups by comparing healthy participants experiencing high pressure (6 kg/cm±0.62) to patients with FM experiencing low pressure (4.5 kg/cm2), NPSp responses for both groups were virtually identical (t 5 0.07, P 5 0.94), suggesting that subjective reports of pain were proportional to pain-specific NPSp responses.

Figure 1C:
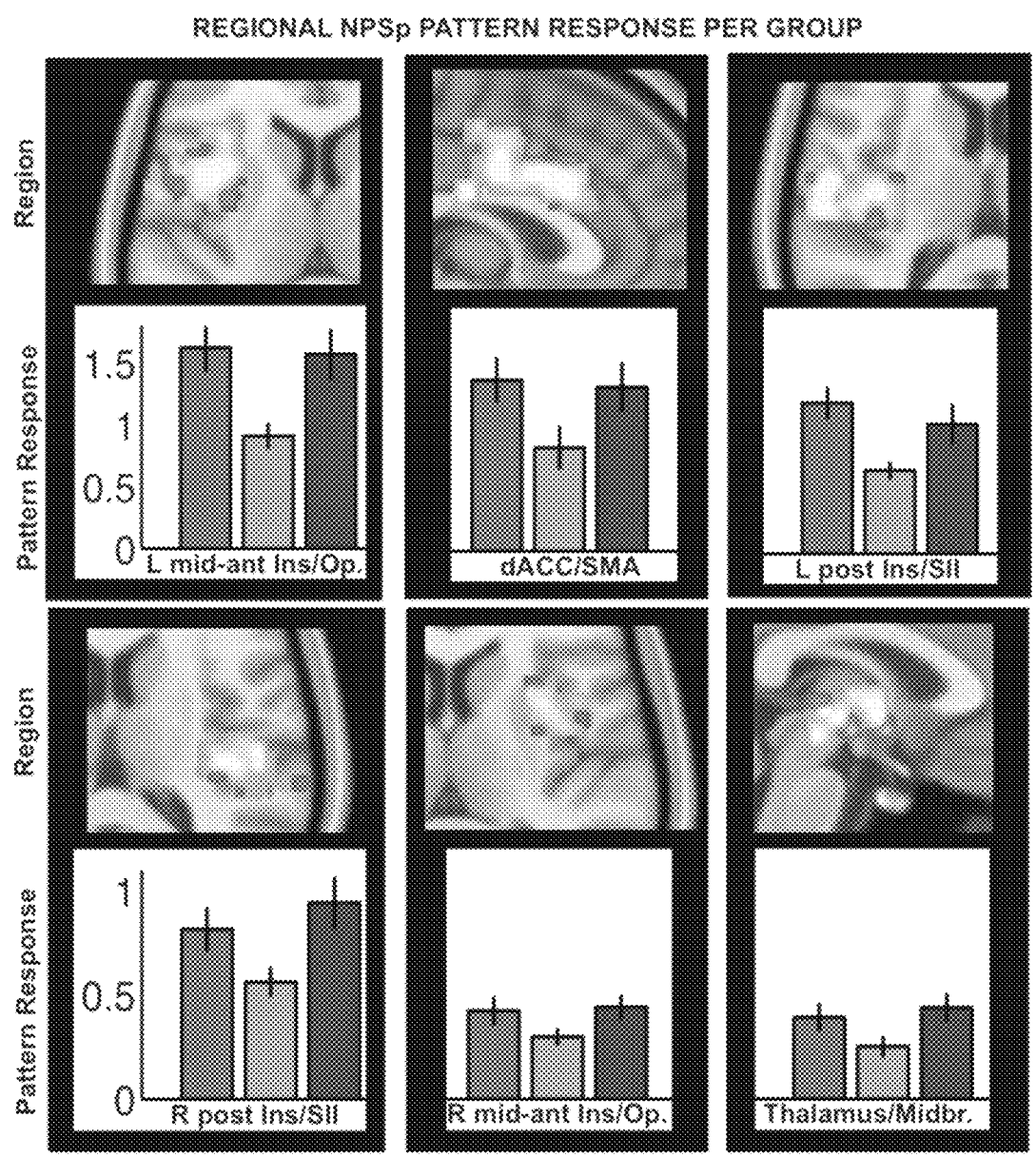
Figure 1D:
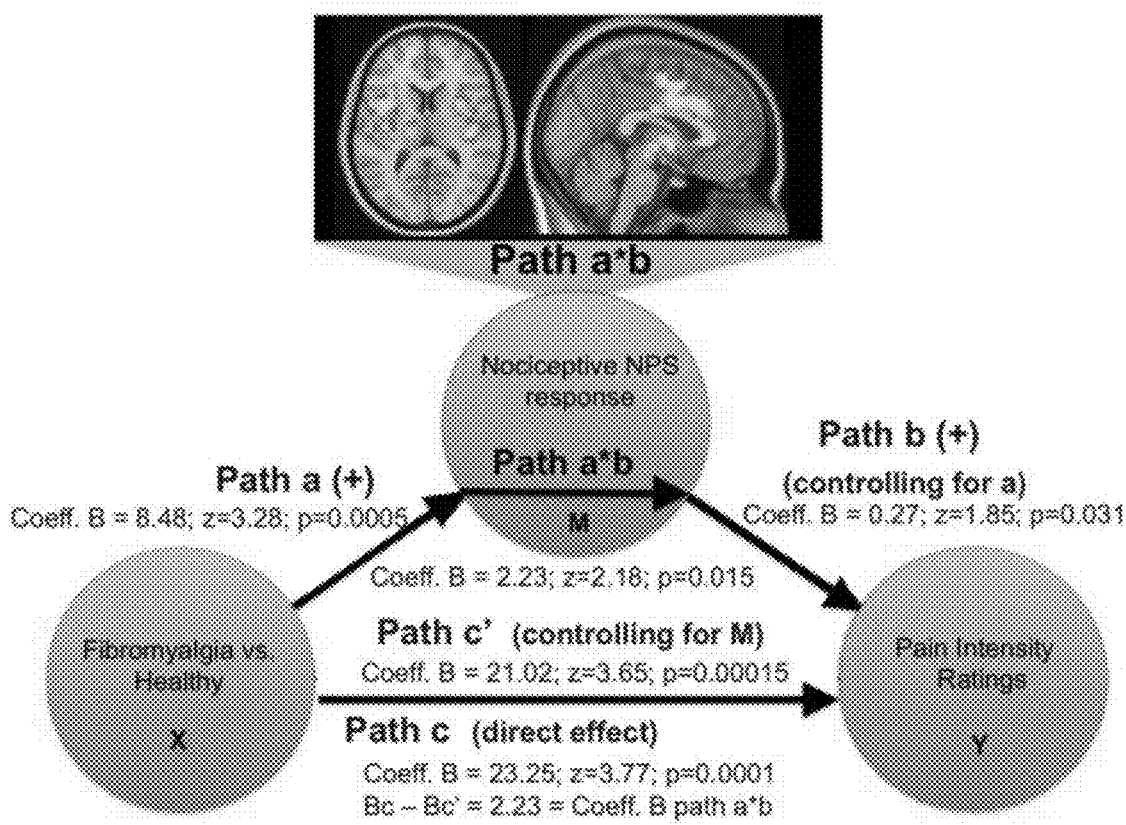
Figure 1E:
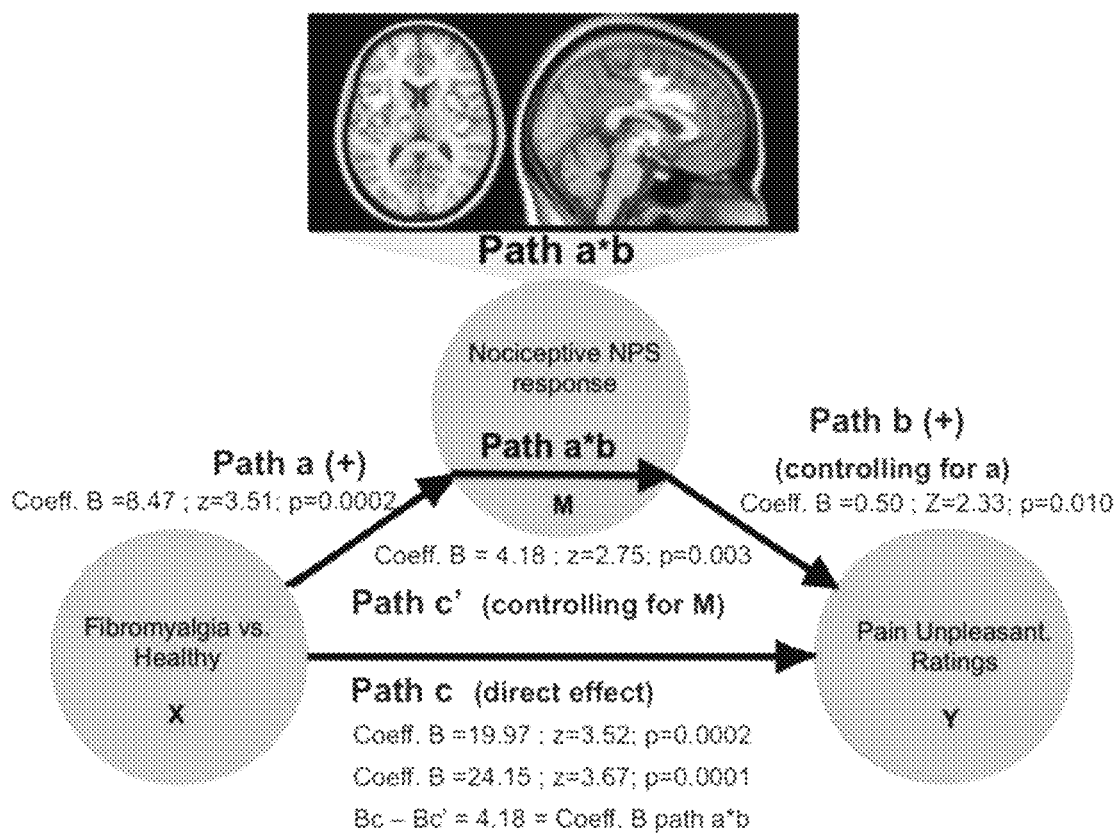

We also examined local signature responses in each contiguous region of the NPSp (FIG. 1C). Comparisons between patients with FM and healthy participants showed significantly greater NPSp responses to low-pressure intensity in patients with FM in all regions tested, with one exception (the inferior frontal gyms). When subjective pain was matched (high pressure in healthy participants vs low pressure in patients with FM), local pattern responses were virtually identical for all regions. Mediation analyses supported the conclusion that FM vs healthy participant difference in pain intensity and unpleasant-ness was significantly partly mediated by NPSp brain responses (FIGS. 1D and 1E).

We also studied pattern responses in the heteromodal regions of the NPSn component, which may have pain modulatory functions but which are not considered nociceptive targets. In the original NPS map, inreased pain was associated with deactivation in these regions. However, NPSn regions in this study showed pain-evoked activation (not deactivation). Patients showed significant pain-evoked activation in both pgACC and PCC/precuneus/paracentral lobule regions of the NPSn, whereas healthy subjects showed significant pain-evoked activation only in the PCC/precuneus/paracentral lobule cluster. For simplicity, pattern response magnitudes are always signed such that increases in pattern response indicate increases in pain activation in these regions. Both patients with FM at low pressure and healthy participants at high pressure showed significant NPSn pattern response (FM: 1.56±1.96 [mean±SD]; t=4.82, P<0.00005; healthy participants, low pressure: 0.30±1.18; t=1.49, P=0.15; healthy participants, high pressure: 1.04±1.61; t=3.40, P=0.0021). Patients with FM showed significantly greater pattern response in NPSn regions than healthy controls (all receiving 4.5 kg/cm2, t=3.27, P=0.002; i.e., greater activation in such regions). Equating pain perception between groups again eliminated the FM vs healthy participant difference (t=1.14, P=0.258). Additionally, in healthy participants, NPSn responses were stronger (i.e., greater activation) in the high-pressure than in the low-pressure condition (t=2.09, P=0.04). Interestingly, the pgACC showed pain-evoked activation only for patients (and not for healthy participants at high pressure). Both NPSn regions (pgACC and PCC/precuneus) exhibited stronger response for patients than healthy participants at matched pressure. Matching pain intensity across groups resulted in statistically equivalent activation in PCC/precuneus but a trend (P=0.100) toward greater activation in the pgACC in patients. Furthermore, there were no between-group differences in pgACC activity between healthy participants at low and high pressure (P=0.48), suggesting that this region does not contribute to pain intensity encoding in healthy participants.

We finally assessed whether the NPSp response to low-pressure intensity performed significantly better than chance in classifying FM status (present vs absent) and found that it classified 68%±5.5 (SE) of the cases correctly (P=0.0029). In addition, NPSn responses to low pressure classified FM status with 71%±5.3 (SE) accuracy (P=0.0004), suggesting that greater pain-evoked activation in NPSn regions at low pressure is an identifying feature of FM. Note the 2 classification accuracy values are not statistically different from each other.

Example 3

Figure 2B:
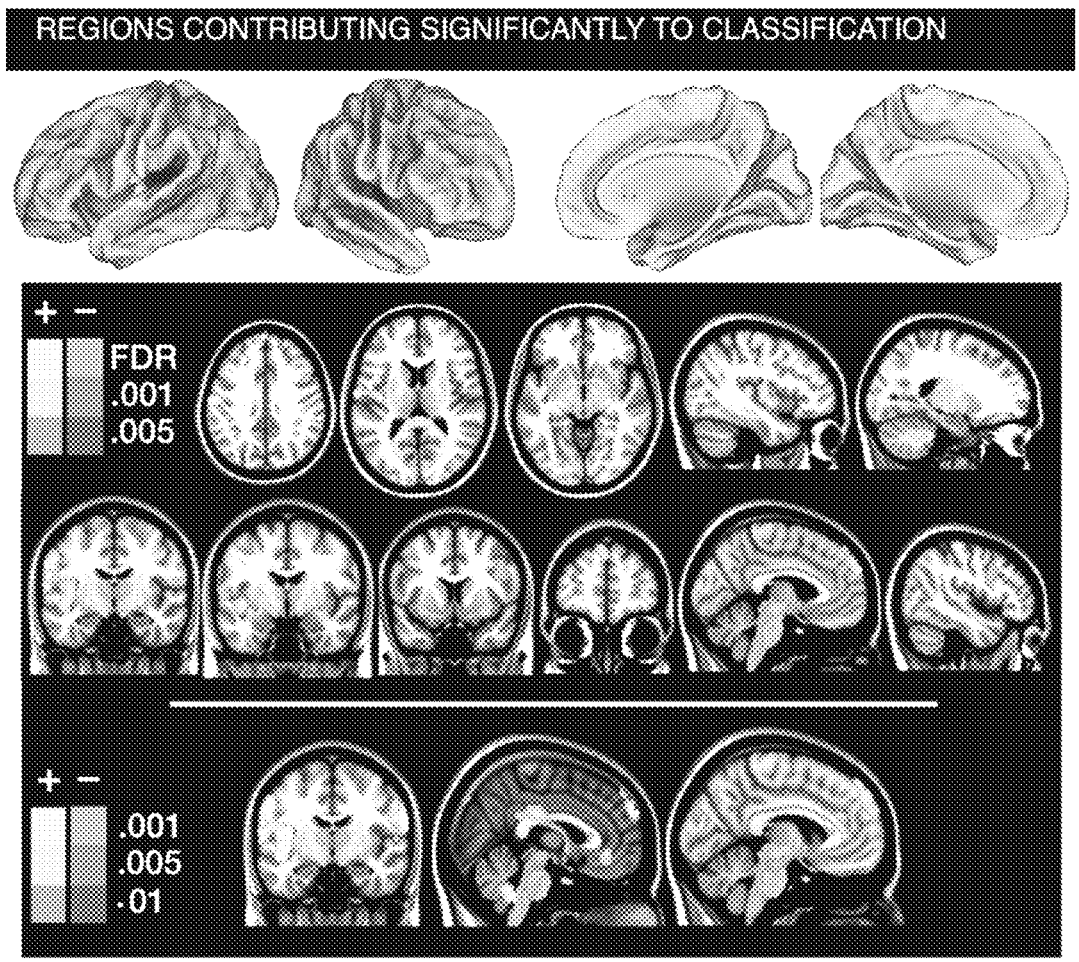

A New Pain-Related Classifier Map (Fibromyalgia-Pain) Discriminates Patients with Fibromyalgia from Controls The FM-pain classification brain pattern (FIGS. 2A and 2B) was characterized by augmented activity in patients with FM in regions associated with sensory integration (second somatosensory cortex (SII)/parietal operculum extending into mid-insula) and self-referential/"default mode" network regions (including dorso-medial prefrontal cortex [PFC; all q<0.05 FDR corrected]). At a lower level of significance (P<0.001), a larger extended network was observed that included augmented pain-related responses in ventromedial PFC/subgenual ACC and PCC. Reduced activity in patients with FM was found in a region considered important for pain and emotion regulation, the dorsolateral PFC (q<0.05 FDR corrected). This pattern, when applied to new test participants, classified patients with FM vs controls with 70%±5.4% accuracy, P=0.0009. Sensitivity was 74% (confidence interval [CI]: 62%-86%) and specificity was 66% (CI: 53%-79%).

Example 4

Figure 3B:
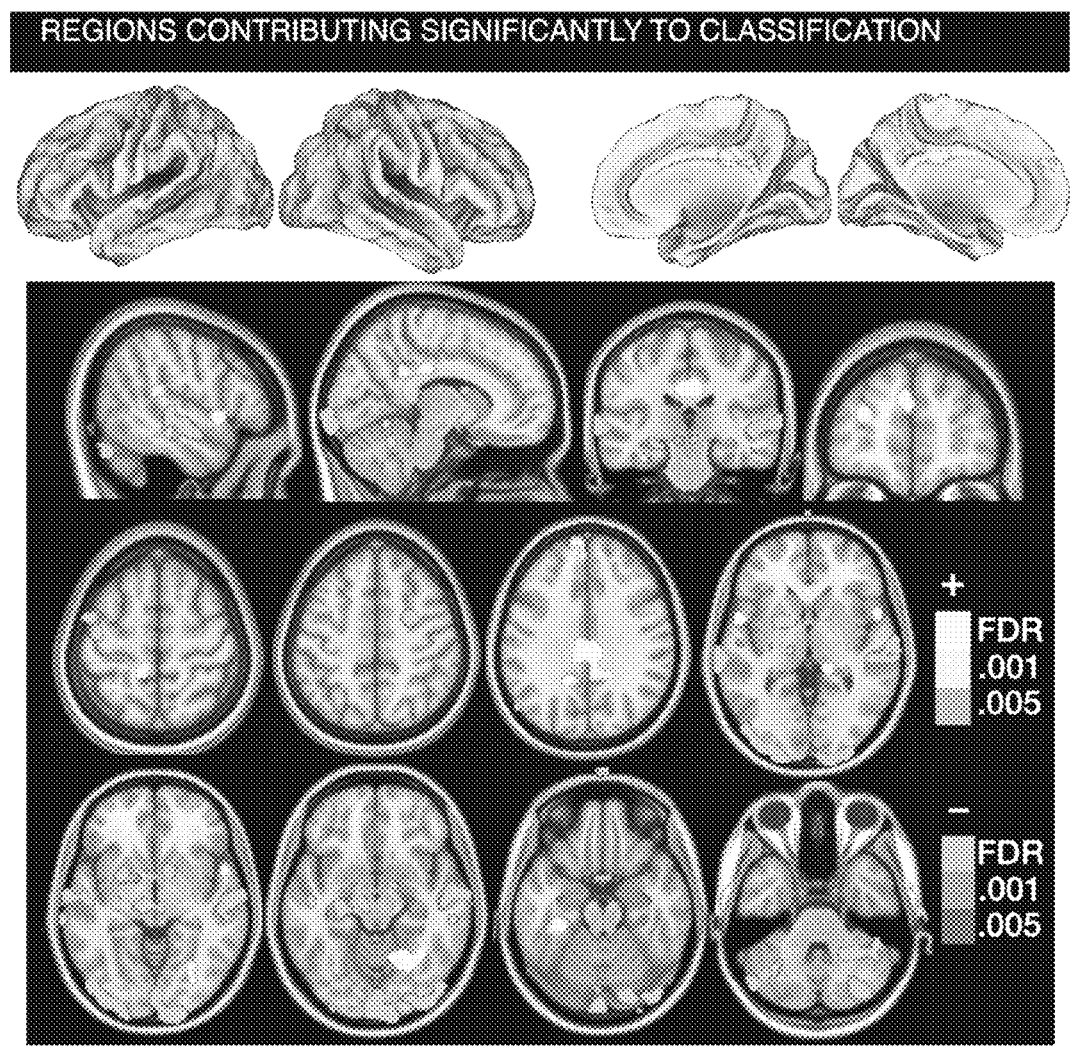

A New Nonpainful Multisensory Classifier Map Discriminates Patients with FM from Controls The multisensory classification pattern (FIGS. 3A and 3B) showed enhanced activity in patients with FM in heteromodal regions associated with multisensory integration (posterior-mid insula/operculum), self-referential/"default mode" network regions (including the PCC/precuneus and dorsomedial PFC), and an anterior lingual region proximal to the parahippocampal gyms. Reduced activity in patients with FM was found in primary/secondary sensory areas (occipital and superior temporal regions) associated with visual and auditory processing, respectively; lateral cerebellum; basal ganglia (dorsal and ventral putamen and pallidum); diencephalon (consistent with subthalamic and hypothalamic regions); dorsolateral PFC; and midbrain. This pattern of activity, when applied prospectively to new test participants, classified patients with FM and healthy participants with a cross-validated accuracy of 89% 6 3.7% (SE), P<0.0000005; sensitivity: 84% (CI: 73%-93%) and specificity: 94% (CI: 87%-100%).

To check for a more global brain functional reorganization in patients with FM, we also tested whether the FM-pain pattern described above could accurately classify patients vs controls using images from the multisensory task and vice versa. Indeed, FM-pain pattern responses computed using individual person—level multisensory contrast images accurately classified FM status (classification accuracy: 86%±4.1%; P<0.0001, sensitivity: 95% [88%-100%], specificity: 77% [64%-88%]). Conversely, multisensory pattern responses computed using individual pressure pain contrast images also classified FM status (classification accuracy: 76%±5.0%; P<0.0001 sensitivity: 65% [CI: 51%-78%], specificity: 89% [CI: 79%-97%]). Thus, the 2 brain classifiers may in part reflect a more general (task≤nonspecific) brain reorganization in FM that is not specific to any one sensory modality.

Example 5

Combined Neural Classifier Using Pain and Multisensory Brain Measures

Figure 4A:
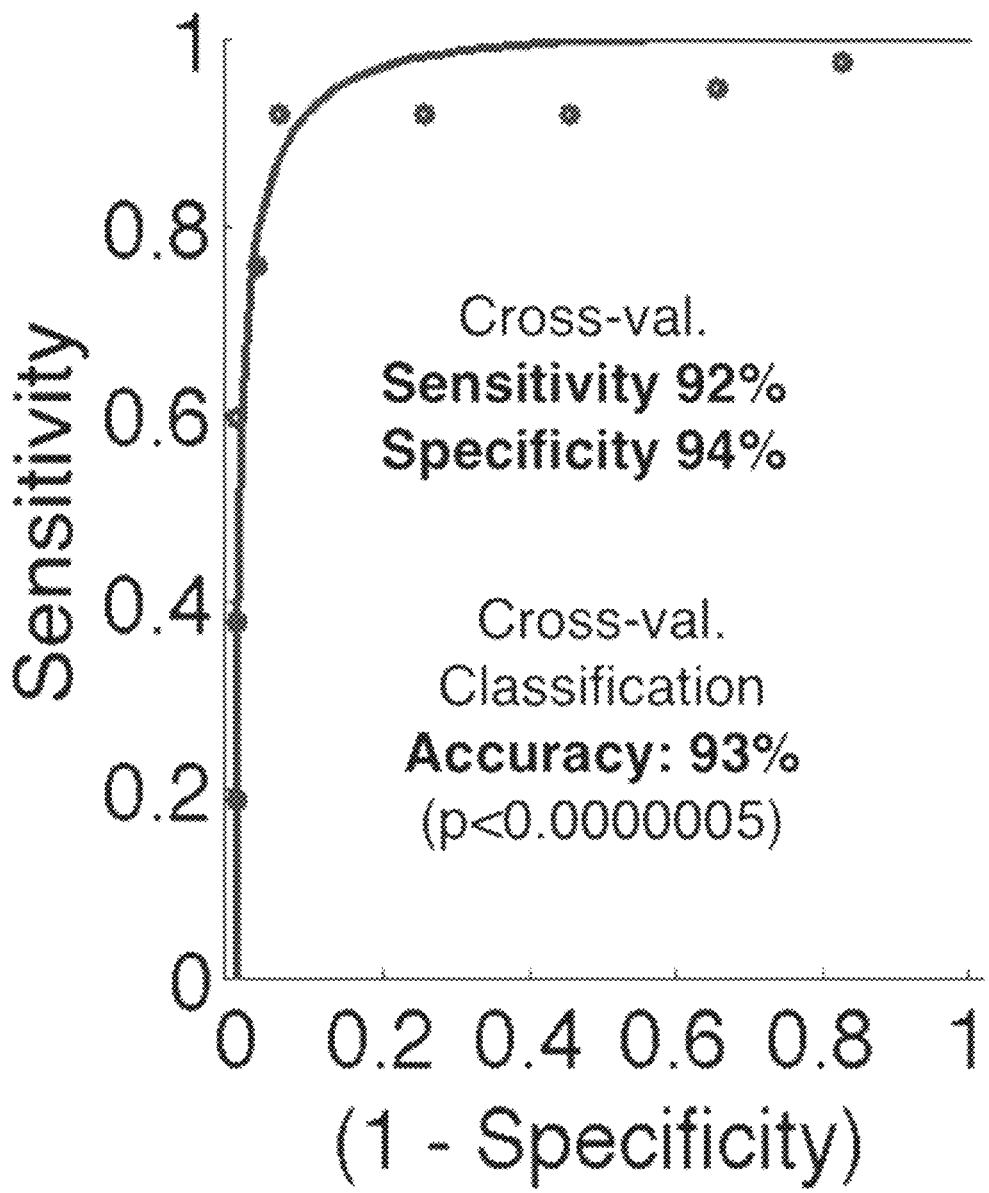
FIGS. 4A and 4B show sensitivity and specificity of the combined neural classifier including nociception-positive neurologic pain signature (NPSp), fibromyalgia (FM)-pain, and multisensory responses (cross-validated) for each subject.
Figure 4B:
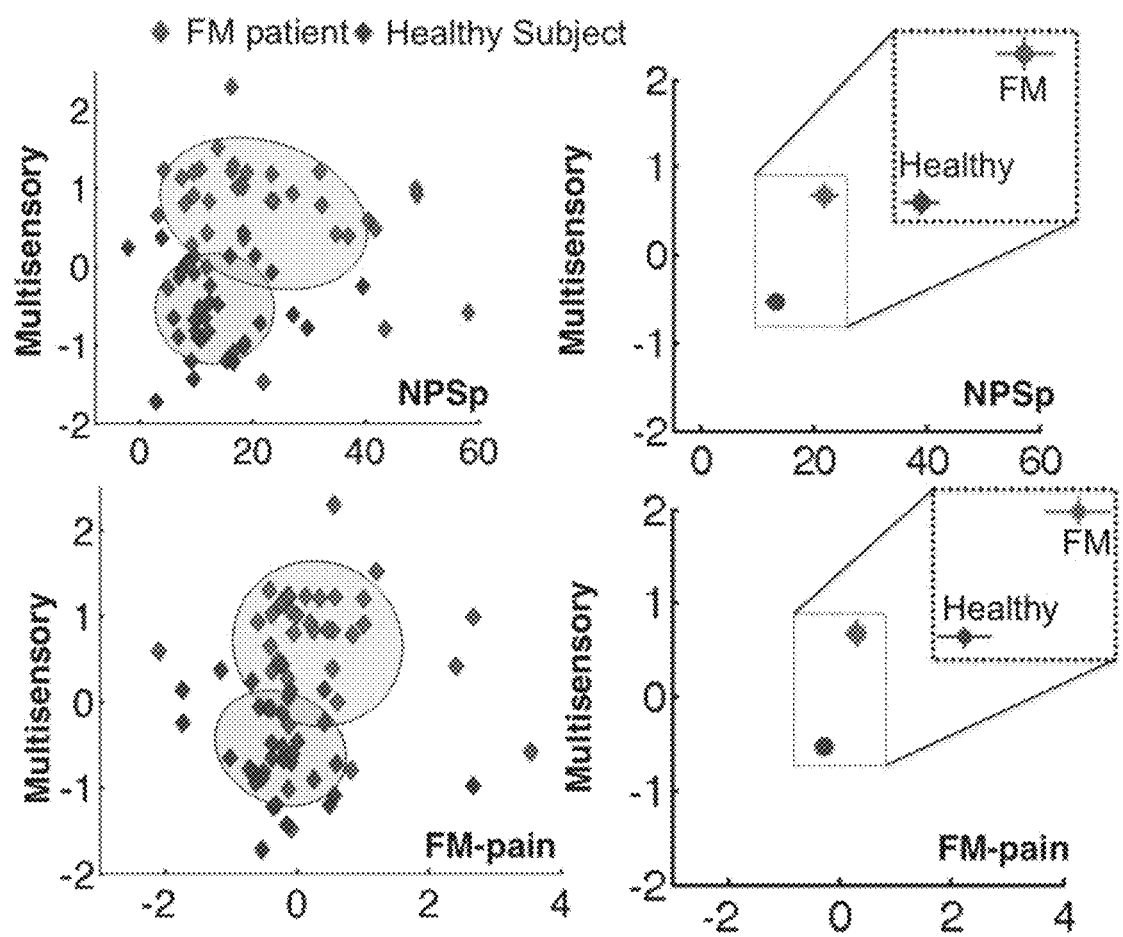

This analysis aimed to predict FM status by combining pattern response values for the NPSp, NPSn, FM-pain, and multisensory patterns using logistic regression. Three of the 4 pattern responses significantly contributed to the prediction of FM status while controlling for the others (NPSp_t=2.16 [P=0.03], FM-pain_t=2.03 [P=0.04], and multisensory_t=4.22 [P<0.0005]), whereas the NPSn was not significant (t=0.09, P=0.924). FIGS. 4A and 4B show the group mean in the joint space of NPSp/FM-pain and multisensory patterns. The combined classifier was able to discriminate patients from healthy participants with a cross-validated accuracy of 93%±3.0% (SE), P<0.0000005; sensitivity: 92% (CI: 84%-98%) and specificity: 94% (CI: 87%-100%).

Example 6

Associations Between Brain Pattern Responses and Medication Status in Patients with FM No significant effect of analgesics (either opioid-dependent [tramadol] or non-opioid dependent [ibuprofen and paracetamol]), hypnotics, or gabapentin was found on pattern response values for any of the 4 brain patterns, i.e., NPSp, NPSn, FM-pain map, and multisensory response (all P>0.10). A significant association was found between anxiolytic/antidepressant medication and NPS measures. Anxiolytic medication (present in 18 out of 37 patients) was significantly associated with NPSn pattern response values (t=2.29, P=0.03), indicating that medicated patients showed greater pain-evoked activation in pgACC and PCC/precuneus regions than patients who were not receiving anxiolytic medication. In addition, antidepressant medication, which is currently prescribed as a standard treatment for FM and was used in 76% of patients in this sample, was associated with greater NPSp (t=3.74, P=0.001) and NPSn responses (i.e., increased activation; t=2.51, P=0.016). These results indicate that patients with FM receiving stable treatment with antidepressants showed significantly greater NPS responses than untreated individuals.

We also found a significant association between antidepressant/anxiolytic medication and clinical severity. Specifically, a variable representing presence of antidepressant/anxiolytic medications (0: no antidepressant neither anxiolytic medication; 1: presence of either antidepressant or anxiolytic medication; and 2: presence of both antidepressant and anxiolytic medication) was positively correlated with HADS depression (r=0.325, P=0.049) and FIQ scores (r=0.341, P=0.039).

Importantly, after controlling for clinical severity (including clinical pain, HADS, and FIQ scores as covariates), the relationship between anxiolytic and antidepressant use and both NPSp and NPSn responses became nonsignificant (all P>0.1). These findings suggest that the observed relationship between medication use and brain measures may reflect common influences of symptom severity on both measures; that is, greater symptom severity is associated with both increased medication use and larger NPS responses.

Example 7

Figure 5:
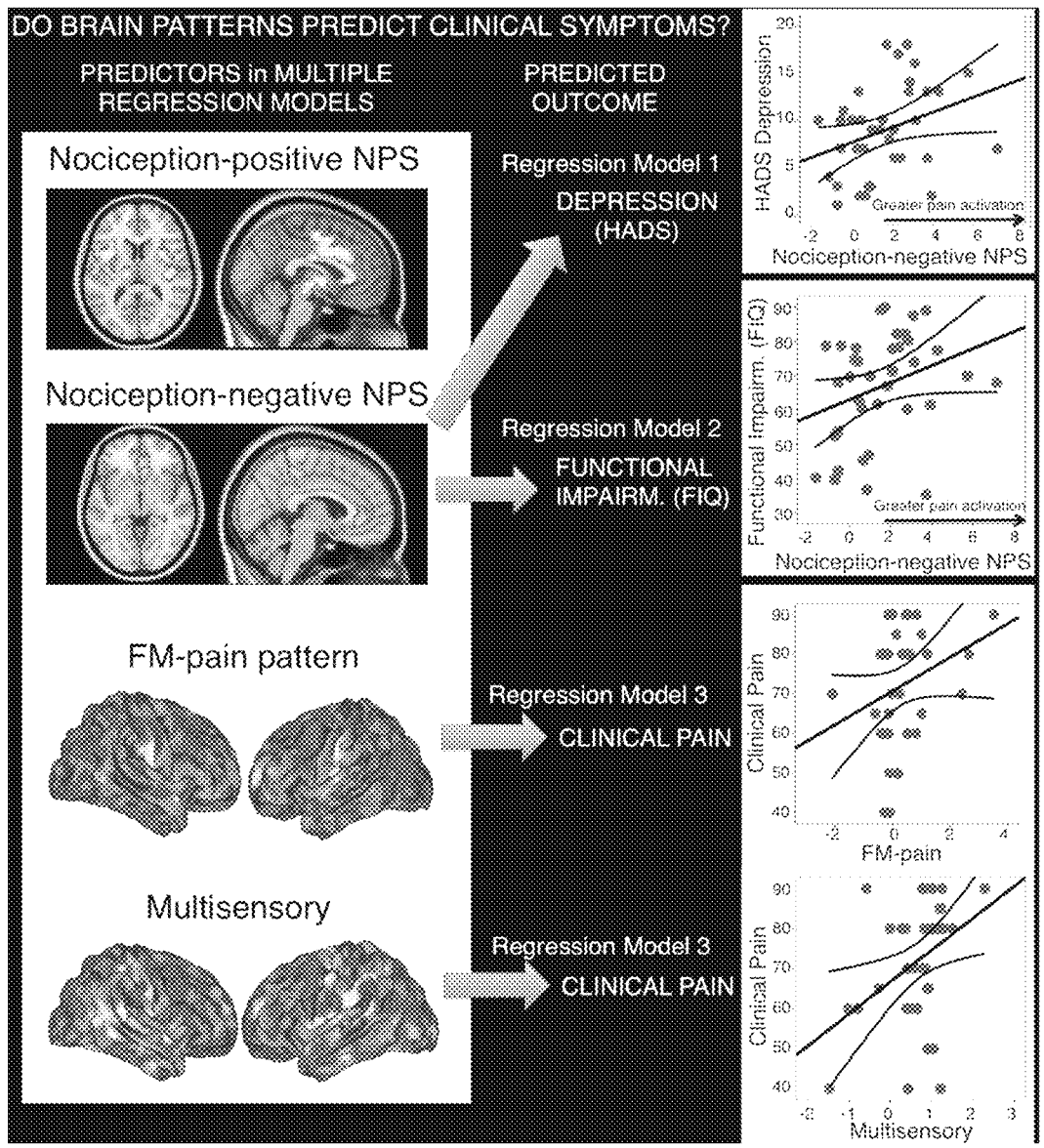
FIG. 5 shows a prediction of symptom severity using brain patterns (nociception-positive neurologic pain signature (NPSp), nociception-negative neurologic pain signature (NPSn), FM-pain, and multisensory) in multiple regression models. The arrows indicate statistically significant predictors for each multiple regression analysis model described in the main text. The straight lines in the plots are the standard linear fit lines for each regression model, and the two additional lines in each plot correspond to the confidence intervals for the mean. Of note, the correlation findings reported here are preliminary and need further replication in multiple samples. The right top panel illustrates the correlation between NPSn pattern responses and Hospital Anxiety and Depression Scale (HADS) depression scores in patients (r=0.333, P=0.044); the next panel illustrates the correlation between NPSn pattern responses and functional impairment scores (r=0.309, P=0.063, 2-tailed); lastly, FM-pain and multisensory responses jointly and significantly contributed to the prediction of clinical pain (main text). Here the raw correlations are provided between clinical pain and FM-pain pattern responses (r=0.279, P=0.094) and clinical pain and multisensory pattern responses (r=0.393, P=0.015). To minimize the influence of potential extreme values while retaining the full sample (which is important for evaluating person-level "signatures"), Spearman rank-correlation tests were also conducted, which revealed the same pattern of results. FIQ, Fibromyalgia Impact Questionnaire.

Associations Between Brain Pattern Responses and Clinical Symptoms in Patients with FM Multiple regression analyses using brain pattern responses (NPSp, NPSn, FM-pain, and multisensory) to predict symptom severity in patients with FM showed that several brain measures correlated with FM symptoms, as illustrated in FIG. 5. In each multiple regression model, we included a predictor representing the presence or absence of anxiolytic/antidepressant medication, to control for medication effects on symptom severity. Greater levels of clinical pain were predicted by a combination of greater FM-pain pattern responses (t=2.14, P=0.039) and greater multisensory pattern responses (t=2.88, P=0.007). The NPSp and NPSn values were not predictive, either individually or in stepwise multiple regression (all P>0.10). Higher FIQ scores (assessing functional impairment associated with the disease) were predicted by a trend toward stronger NPSn responses (t=1.92, P=0.06), indicating that greater pain-evoked activation in NPSn regions was associated with marginally greater FIQ scores. Other measures were not predictive, either alone or in stepwise regression (all P>0.10). Greater depressive symptomatology (HADS depression) was also predicted by stronger NPSn responses (t=2.09, P=0.04) but not by other measures (all P>0.10). Our correlation findings are preliminary and need further replication in larger samples.

Example 8

Brain Pattern Responses and Time Since Diagnosis

There was no significant association between time since diagnosis (surrogate measure for time exposed to the disorder) and brain pattern responses (NPS, FM-pain, and multisensory: P>0.1).

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed is:

1. A method of detecting fibromyalgia (FM) in a subject comprising:
   applying a stimulus to a subject known to have FM, wherein the stimulus is a non-painful, multisensory stimulus comprising visual, auditory, and tactile-motor stimulation;
   detecting brain activity of the subject known to have FM in response to the stimulus using functional Magnetic Resonance Imaging (fMRI) and generating a neurologic signature map of brain activity indicative of FM in response to the stimulus;

applying a stimulus to a patient suspected of having FM, wherein the stimulus is selected from at least one of:
a non-painful, multisensory stimulus comprising visual, auditory, and tactile-motor stimulation;
detecting brain activity of the patient in response to the stimulus using fMRI and generating a brain map of the patient representing the brain activity of the patient in response to the stimulus;
comparing the brain map of the patient to said neurologic signature map indicative of FM; and,
diagnosing FM in the patient if the brain map of the patient is at least 70% identical to said neurologic signature map indicative of FM.

2. The method of claim 1, and further comprising wherein the neurologic signature map indicative of FM comprises an fMRI pattern created in a subject known to have FM in response to pain created by the application of pressure pain stimulus comprising applying pressure to a surface of the subject and that is at least 70% identical to the Nociception-Positive NPS (NPSp) Pattern Of Voxel Weights.

3. The method of claim 2, wherein the applied pressure is 4.5 kg/cm$^2$.

4. The method of claim 2, wherein the fMRI pattern is created by detecting brain activity in the subject known to have FM in brain regions of major targets of ascending nociceptive afferents selected from the group consisting of: the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof.

5. The method of claim 1, wherein the neurologic signature map indicative of FM comprises an fMRI pattern created in a subject known to have FM in response to pain created by the application of pressure to a surface of the subject and that is at least 70% identical to the fMRI FM-Pressure Pain Pattern.

6. The method of claim 5, wherein the applied pressure is 4.5 kg/cm$^2$.

7. The method of claim 1, wherein the neurologic signature map indicative of FM comprises an fMRI pattern created in a subject known to have FM in response to simultaneous presentation of visual, auditory, and tactile stimulation and that is at least 70% identical to the fMRI Multisensory Pattern.

8. The method of claim 7, wherein the simultaneous presentation of visual, auditory, and tactile stimulation comprises the simultaneous presentation of a full-field flashing light, a series of auditory tones presented at a temporal frequency, and repeated touching of the subject's fingers.

9. The method of claim 1, wherein the brain map of the patient is compiled based on activation patterns in brain regions of major targets of ascending nociceptive afferents selected from the group consisting of: the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof, during painful pressure and analyzed using linear support vector machines, and the neurological signature map is at least 70% identical to the FM-Pressure Pain Pattern.

10. The method of claim 1, wherein the brain map of the patient is compiled based on whole-brain activation patterns during non-painful multisensory stimulation analyzed using linear support vector machines and the signature map is at least 70% identical to the Multisensory Pattern.

11. The method of claim 2, wherein the brain map of the patient is compiled using logistic regression to combine each of:
a) an fMRI pattern created in the brain of the patient in response to pain created by the application of pressure to a patient of the subject; and
b) an fMRI pattern created in the patient in brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof, during painful pressure and analyzed using linear support vector machines; and
c) an fMRI pattern created in the brain of the patient in response to non-painful multisensory stimulation analyzed using linear support vector machines.

12. The method of claim 11, wherein the neurologic signature map indicative of FM is compiled using logistic regression to combine each of:
a) an fMRI pattern created in the brain of a subject known to have FM in response to pain created by the application of pressure to a surface of the subject; and
b) an fMRI pattern created in a subject known to have FM in brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof, during painful pressure and analyzed using linear support vector machines; and
c) an fMRI pattern created in the brain of a subject known to have FM in response to non-painful multisensory stimulation analyzed using linear support vector machines.

13. The method of claim 1, wherein the method comprises applying the neurologic signature map to the brain map of the patient to provide a response value.

14. The method of claim 1, wherein the method comprises analyzing similarities and dissimilarities between portions of the brain map of the patient and the corresponding portions of the neurologic signature map indicative of FM.

15. The method of claim 1, wherein the patient is diagnosed with FM when at least one brain map of the patient is at least 90% identical to the neurologic signature map indicative of FM.

16. The method of claim 1, wherein the patient is human.

17. The method of claim 1, wherein the patient is diagnosed with FM based on comparison of the brain map of the patient to the neurologic signature map indicative of FM and in conjunction with at least one of heart rate variability and fitness test results for the patient.

18. The method of claim 1, and further comprising applying a stimulus to a patient suspected of having FM, wherein the stimulus is pressure pain stimulus.

19. A method of evaluating the efficacy of a putative treatment of fibromyalgia (FM) in a subject comprising:
a. applying a stimulus to the subject, wherein the stimulus is selected from at least one of:
i. a pressure pain stimulus, and
ii. a non-painful, multisensory stimulus comprising visual, auditory, and tactile-motor stimulation;

b. detecting brain activity of the subject in response to the stimulus using functional Magnetic Resonance Imaging (fMRI) and generating a brain map of the subject representing the brain activity of the subject in response to the stimulus;

c. comparing the brain map of the subject to a neurologic signature map, wherein the neurologic signature map represents brain activity indicative of FM in the subject;

d. administering a putative treatment of FM to the subject;

e. applying a stimulus to the subject, wherein the stimulus is selected from at least one of:
   i. a pressure pain stimulus, and
   ii. a non-painful, multisensory stimulus comprising visual, auditory and tactile-motor stimulation;

f. detecting brain activity of the subject in response to the stimulus using fMRI and generating a brain map of the subject representing the brain activity of the subject in response to the stimulus;

g. comparing the brain map of the subject to a neurologic signature map, wherein the neurologic signature map represents brain activity indicative of FM in the subject;

h. evaluating the putative treatment to be efficacious in the treatment of FM if the subject's brain map created prior to administration of the putative treatment is more similar to the neurologic signature map than after the administration of the putative treatment.

20. A fibromyalgia (FM) evaluation system comprising:
a memory operable to store magnetic resonance imaging (MRI) data content;
a processor in communication with the memory, the processor operable to:
execute an analysis of stored data operable to:
  compare functional magnetic resonance image (fMRI) data content for two or more MRI data sets;
  determine data characteristics in one or more MRI data sets; and
  receive a criteria to sort the two or more MRI data sets, wherein the criteria comprises:
    1) fMRI analysis of a subject receiving a pressure pain stimulus;
    2) fMRI analysis of brain regions of major targets of ascending nociceptive afferents selected from the group consisting of the thalamus, primary and secondary somatosensory regions (SI/SII), posterior, mid and anterior insula and adjacent opercula, midbrain, dorsal anterior cingulate cortex, inferior frontal gyrus, amygdala, and combinations thereof in a subject receiving a pressure pain stimulus; and
    3) fMRI analysis of a subject receiving non-painful, multisensory stimulus; and
execute a user interface application in communication with the MRI data service, the user interface application operable to provide a first view of two or more thumbnails associated with each of the MRI data sets based on the data characteristic and the criteria, wherein the first view includes two or more thumbnails associated with the two or more MRI data sets.

* * * * *